United States Patent
Mao et al.

(10) Patent No.: US 10,253,344 B2
(45) Date of Patent: Apr. 9, 2019

(54) RECOMBINANT PRODUCTION OF STEVIOL GLYCOSIDES

(71) Applicant: Conagen Inc., Bedford, MA (US)

(72) Inventors: Guohong Mao, Burlington, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 15/631,083

(22) Filed: Jun. 23, 2017

(65) Prior Publication Data

US 2017/0298404 A1    Oct. 19, 2017

Related U.S. Application Data

(62) Division of application No. 15/032,286, filed as application No. PCT/US2014/059081 on Oct. 3, 2014.

(60) Provisional application No. 61/898,571, filed on Nov. 1, 2013.

(51) Int. Cl.

| | |
|---|---|
| *C12P 19/56* | (2006.01) |
| *A23L 2/60* | (2006.01) |
| *A21D 13/06* | (2017.01) |
| *A23G 3/38* | (2006.01) |
| *C12N 9/10* | (2006.01) |
| *A23G 3/36* | (2006.01) |
| *A23G 4/06* | (2006.01) |
| *A23L 27/30* | (2016.01) |
| *C12N 15/52* | (2006.01) |
| *A23L 33/105* | (2016.01) |
| *A21D 13/062* | (2017.01) |
| *C07H 15/24* | (2006.01) |

(52) U.S. Cl.
CPC ............ *C12P 19/56* (2013.01); *A21D 13/062* (2013.01); *A23G 3/36* (2013.01); *A23G 3/38* (2013.01); *A23G 4/06* (2013.01); *A23L 2/60* (2013.01); *A23L 27/33* (2016.08); *A23L 27/36* (2016.08); *A23L 33/105* (2016.08); *C07H 15/24* (2013.01); *C12N 9/1048* (2013.01); *C12N 9/1051* (2013.01); *C12N 9/1062* (2013.01); *C12N 15/52* (2013.01); *C12Y 204/01* (2013.01); *A23V 2002/00* (2013.01); *C12Y 204/00* (2013.01)

(58) Field of Classification Search
CPC ......... C12P 19/56; A23G 3/38; C12N 9/1048; C12Y 204/00
USPC ...................................... 435/78, 320.1, 69.1
See application file for complete search history.

(56) References Cited

U.S. PATENT DOCUMENTS

| | | |
|---|---|---|
| 2013/0171328 A1 | 7/2013 | Kishore et al. |
| 2016/0251635 A1 | 9/2016 | Mao et al. |
| 2017/0081691 A1 | 3/2017 | Mao et al. |

FOREIGN PATENT DOCUMENTS

| | | |
|---|---|---|
| WO | WO 2013/022989 A2 | 2/2013 |
| WO | WO 2015/065650 A2 | 5/2015 |
| WO | WO 2015/065650 A3 | 5/2015 |

OTHER PUBLICATIONS

GenBank entry AK367039 [http://www.ncbi.nlm.nih.gov/nuccore/AK367039] May 20, 2011 (retrieved Feb. 24, 2015).
Kovylyaeva et al., Glycosides from Stevia rebaudiana. Chem Natural Compounds. Jan. 2007;43(1):81-85.
Matsumoto et al., Comprehensive sequence analysis of 24,783 barley full-length cDNAs derived from 12 clone libraries. Plant Physiol. May 2011;156(1):20-8. doi:10.1104/pp.110.171579.
Meech et al., The glycosidation of xenobiotics and endogenous compounds: versatility and redundancy in the UDP glycosyltransferase superfamily. Pharmacol Ther. May 2012;134(2):200-18. doi:10.1016/j.pharmthera.2012.01.009. Epub Feb. 1, 2012.
UniProtKB Accession No. F2DT21. May 31, 2011.
Woelwer-Rieck et al., Improved HPLC method for the evaluation of the major steviol glycosides in leaves of Stevia rebaudiana. European Food Res Tech. Aug. 2010;231(4):581-588.
Devos et al., Practical limits of function prediction. Proteins. Oct. 1, 2000;41(1):98-107.
Kisselev, Polypeptide release factors in prokaryotes and eukaryotes: same function, different structure. Structure. Jan. 2002;10(1):8-9.
Whisstock et al., Prediction of protein function from protein sequence and structure. Q Rev Biophys. Aug. 2003;36(3):307-40.
Witkowski et al., Conversion of a beta-ketoacyl synthase to a malonyl decarboxylase by replacement of the active-site cysteine with glutamine. Biochemistry. Sep. 7, 1999;38(36):11643-50.
PCT/US2014/059081, May 3, 2016, International Preliminary Report on Patentability.
PCT/US2014/059081, Mar. 23, 2015, International Search Report and Written Opinion.
EP 14857965.9, May 18, 2017, Extended European Search Report.

*Primary Examiner* — Robert B Mondesi
*Assistant Examiner* — Mohammad Y Meah
(74) *Attorney, Agent, or Firm* — Wolf, Greenfield & Sacks, P.C.

(57) ABSTRACT

Recombinant polypeptides having UDP-glycosyltransferase activities, including a 1,2-19-O-glucose glycosylation activity and a 1,2-13-O-glucose glycosylation activity for synthesizing of steviol glucosides, are provided. A method of producing a steviol glycoside composition using such recombinant polypeptide is also provided. Also disclosed are steviol glycosides referred to as rebaudioside Z1 and rebaudioside Z2.

15 Claims, 14 Drawing Sheets

Specification includes a Sequence Listing.

RECOMBINANT PRODUCTION OF STEVIOL GLYCOSIDES

CROSS-REFERENCE TO RELATED APPLICATIONS

This application is a divisional of U.S. application Ser. No. 15/032,286, filed Apr. 26, 2016, now abandoned, which is a 35 U.S.C. § 371 National Phase Application of International Application No. PCT/US2014/059081, filed Oct. 3, 2014, which claims priority to U.S. Provisional Patent Application No. 61/898,571, filed on Nov. 1, 2013, the contents of each of which are hereby incorporated by reference in their entirety.

INCORPORATION OF SEQUENCE LISTING

A computer readable form of the Sequence Listing contained in the file named C149770010US03-SEQ-AM.txt and created on Jun. 22, 2017, which is 46,861 bytes in size (as measured in Microsoft WINDOWS® Explorer), is provided herein and is herein incorporated by reference. This Sequence Listing consists of SEQ ID NOs: 1-12.

BACKGROUND

The present disclosure relates generally to the biosynthesis of steviol glycosides. In particular, the present disclosure relates to a recombinant polypeptide that catalyzes the production of steviol glycosides such as rebaudioside D, rebaudioside E and a novel rebaudioside (rebaudioside Z).

Steviol glycosides are natural products isolated from *Stevia rebaudiana* leaves, and are widely used as high intensity, low-calorie sweeteners. Naturally occurring steviol glycosides have the same base structure (steviol) and differ in the content of carbohydrate residues (e.g. glucose, rhamnose, and xylose residues) at the C13 and C19 positions. Steviol glycosides with known structure include stevioside, rebaudioside A, rebaudioside B, rebaudioside C, rebaudioside D, rebaudioside E, rebaudioside F, and dulcoside A.

On dry weight basis, stevioside, rebaudioside A, rebaudioside C, and dulcoside A, account for 9.1, 3.8, 0.6, and 0.3% of the total weight of the steviol glycosides in the leaves, respectively, while the other steviol glucosides are present in much lower amounts. Extracts from *Stevia rebaudiana* plant are commercially available, which typically contain stevioside and rebaudioside A as primary compounds. The other steviol glycosides typically are present in the *stevia* extract as minor components. For example, the amount of rebaudioside A in commercial preparations can vary from about 20% to more than 90% of the total steviol glycoside content, while the amount of rebaudioside B can be about 1-2%, the amount of rebaudioside C can be about 7-15%, and the amount of rebaudioside D can be about 2% of the total steviol glycosides.

As natural sweeteners, different steviol glucosides have different degrees of sweetness and after-taste. The sweetness of steviol glycosides is significantly higher than that of sucrose. For example, stevioside is 100-150 times sweeter than sucrose with bitter after-taste, while rebaudioside A and E are 250-450 times sweeter than sucrose and the after-taste is much better than stevioside. Accordingly, the taste profile of any *stevia* extract is profoundly affected by the relative content of the steviol glycosides in the extract, which in turn may be affected by the source of the plant, the environmental factors (such as soil content and climate), and the extraction process. In particular, variations of the extraction conditions can lead to inconsistent compositions of the steviol glycosides in the *stevia* extracts, such that the taste profile varies among different batches of extraction products. The taste profile of *stevia* extracts also can be affected by plant-derived contaminants (such as pigments, lipids, proteins, phenolics, and saccharides) that remain in the product after the extractions process. These contaminants typically have off-flavors undesirable for the use of the *stevia* extract as a sweetener.

The majority of the steviol glycosides are formed by several glycosylation reactions of steviol, which typically are catalyzed by the UDP-glycosyltransferases (UGTs) using uridine 5'-diphosphoglucose (UDP-glucose) as a donor of the sugar moiety. In plants, UGTs are a very divergent group of enzymes that transfer a glucose residue from UDP-glucose to steviol. Stevioside is an intermediate in the biosynthesis of rebaudioside compounds. For example, glycosylation of the C-3' of the C-13-O-glucose of stevioside yields rebaudioside A; and glycosylation of the C-2' of the 19-O-glucose of the stevioside yields rebaudioside E. Further glycosylation of rebaudioside A (at 19-O-glucose) or rebaudioside E (at C-13-O-glucose) produces rebaudioside D. (FIGS. 1A-1C).

A practical approach to improve the taste quality of *stevia* extract is to increase the yield of rebaudioside compounds by further glycosylation of stevioside. The UGTs with a 1,2-19-O-glucose glycosylation activity are important enzymes for rebaudioside D and E production.

Sucrose synthases (SUS) catalyze the conversion of the UDP to UDP-glucose in the presence of sucrose. Thus, for a glycosylation reaction utilizing UDP-glucose (such as those catalyzed by the UGTs), SUS can be used to re-generate UDP-glucose from UDP, enhancing the efficiency of such reaction (FIG. 2).

Accordingly, there is a need for steviol glycosides with consistent taste profile and less off-flavor than the existing commercial products. As described herein, the present disclosure provides a recombinant polypeptide that is useful for preparing steviol glycosides (such as rebaudioside D and rebaudioside E). The present disclosure also provides a method of producing a steviol glycoside (rebaudioside Z) composition using such recombinant polypeptide.

BRIEF DESCRIPTION

The subject technology generally relates to recombinant polypeptides that have UDP-glycosyltransferase activities. In particular, polypeptides having a 1,2-19-O-glucose glycosylation activity for steviol glycoside compounds are provided. In one aspect, the subject technology relates to a recombinant polypeptide comprising an amino acid sequence having at least 80% identity to SEQ ID NO:6. In an exemplary embodiment, the amino acid sequence of the recombinant polypeptide described herein has at least 85%, at least 90%, at least 91%, at least 92%, at least 93%, at least 94%, at least 95%, at least 96%, at least 97%, at least 98%, at least 99%, or even 100% identity to SEQ ID NO:6.

In another aspect, the subject technology relates to an isolated nucleic acid comprising a nucleotide sequence encoding the recombinant polypeptide described herein. In another aspect, the subject technology relates to a vector comprising the nucleic acid described herein, and a host cell comprising the vector described herein. In an exemplary embodiment, the host cell of the subject technology is selected from the group consisting of bacteria, yeast, filamentous fungi, cyanobacteria algae and plant cell.

In another aspect, the subject technology also relates to a method of producing a steviol glycoside composition, the method comprising incubating a substrate (such as stevioside, rebaudioside A, rebaudioside E or a combination thereof) with a recombinant polypeptide comprising an amino acid sequence having at least 80% identity to SEQ ID NO:6. In an exemplary embodiment, the amino acid sequence of the recombinant polypeptide used in the method described herein has at least 85%, at least 90%, at least 91%, at least 92%, at least 93%, at least 94%, at least 95%, at least 96%, at least 97%, at least 98%, at least 99%, or even 100% identity to SEQ ID NO:6.

In another aspect, the subject technology also relates to a method of producing a steviol glycoside composition, the method comprising incubating a substrate (such as stevioside and rebaudioside E) with a recombinant polypeptide comprising an amino acid sequence having at least 80% identity to SEQ ID NO:11. In an exemplary embodiment, the amino acid sequence of the recombinant polypeptide used in the method described herein has at least 85%, at least 90%, at least 91%, at least 92%, at least 93%, at least 94%, at least 95%, at least 96%, at least 97%, at least 98%, at least 99%, or even 100% identity to SEQ ID NO:11.

In one embodiment, the method further comprises incubating a recombinant sucrose synthase (such as one with an amino acid sequence having at least 80% identity to the amino acid sequence of AtSUS1 as set forth in SEQ ID NO:9) with the substrate and the recombinant polypeptide described herein. In another embodiment, the method further comprises incubating a recombinant UDP-glycosyltransferase (such as one with an amino acid sequence having at least 80% identity to the amino acid sequence of UGT76G1 as set forth in SEQ ID NO:11) with the recombinant sucrose synthase, the substrate, and the recombinant polypeptide described herein. In another embodiment, the method described herein comprises incubating the substrate with a host cell expressing the recombinant polypeptide.

The subject technology also relates to a novel steviol glycoside, termed rebaudioside Z, which is characterized by a retention time of about 6.68 minutes on a HPLC under conditions described herein. The subject technology also relates to a method of producing rebaudioside Z described herein, the method comprising incubating a substrate with a recombinant polypeptide comprising an amino acid sequence having at least 80% identity to SEQ ID NO:6. As used herein, the terms "rebaudioside Z" or "Reb Z" refer to a mixture of compounds, particularly, a mixture of rebaudioside Z1 ("Reb Z1") and rebaudioside Z2 ("Reb Z2").

In one embodiment, the present disclosure is further directed to a method for synthesizing rebaudioside Z from rebaudioside E. The method includes: preparing a reaction mixture comprising rebaudioside E, a substrate selected from the group consisting of sucrose, uridine diphosphate (UDP) and uridine diphosphate-glucose (UDP-glucose), and HV1, and sucrose synthase, incubating the reaction mixture for a sufficient time to produce rebaudioside Z, wherein a glucose is covalently coupled to the rebaudioside E to produce rebaudioside Z, a glucose is covalently coupled to the C2'-13-O-glucose of rebaudioside E to produce rebaudioside Z1, and a glucose is covalently coupled to C2'-19-O-glucose of rebaudioside E to produce rebaudioside Z2.

In one embodiment, the rebaudioside Z compound is rebaudioside Z1 (Reb Z1) having the structure:

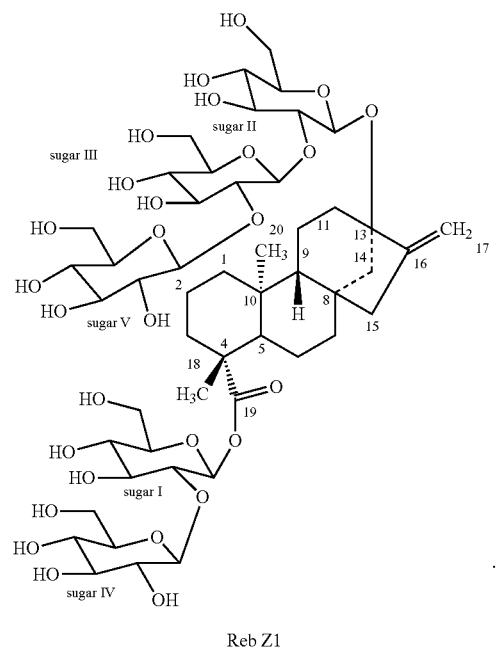

Reb Z1

In one embodiment, the rebaudioside Z compound is rebaudioside Z2 (Reb Z2) having the structure:

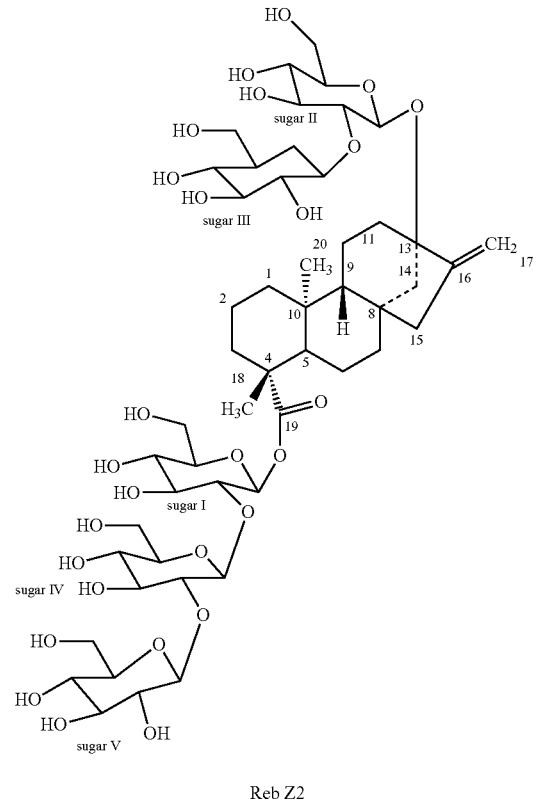

Reb Z2

As described herein, the recombinant polypeptides of the present technology are useful for developing a biosynthetic method for preparing steviol glycosides that are typically of low abundance in natural sources, such as rebaudioside D and rebaudioside E. Accordingly, the present technology also provides for a steviol glycoside composition produced by the biosynthetic method described herein. Such composition can comprise a steviol glycoside compound selected from the group consisting of rebaudioside D, rebaudioside E, a novel rebaudioside (referred to herein as "rebaudioside Z" and "Reb Z") and combinations thereof. Further, a sweetener comprising the steviol glycoside composition described herein is also provided.

In one embodiment, the present disclosure is directed to a sweetener including a compound having the chemical structure:

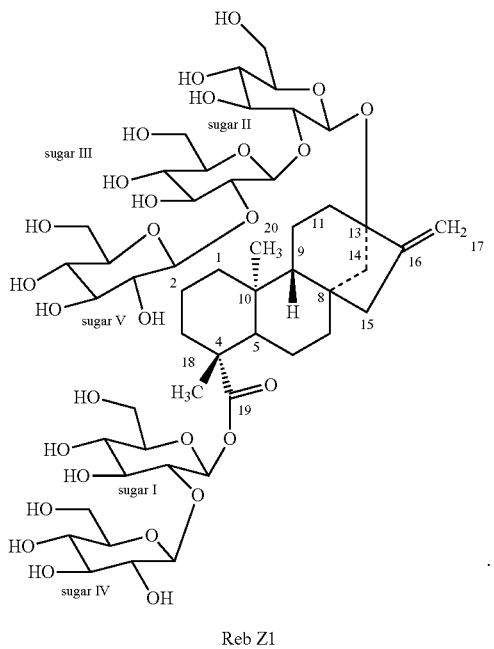

Reb Z1

In another embodiment, the sweetener includes a compound having the chemical structure:

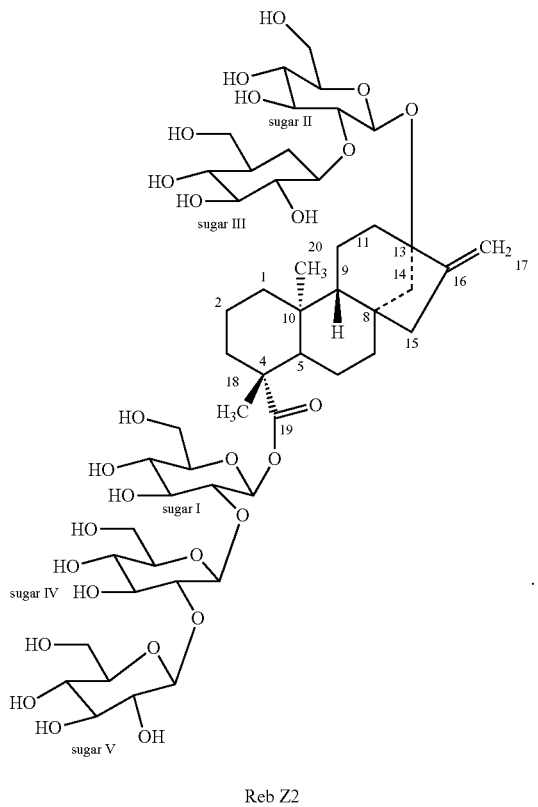

Reb Z2

The present disclosure is further directed to using the sweeteners in consumable products such as beverages, confectioneries, bakery products, cookies, and chewing gums.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1C also show that a recombinant UGT76G1 enzyme ("UGT76G1", different from the recombinant HV1 polypeptide) catalyzes the reaction that transfers a sugar moiety to C-3' of the C-13-O-glucose of stevioside to produce rebaudioside A, or similarly to produce rebaudioside D from rebaudioside E.

FIG. 3A shows the standards of stevioside ("Ste"), Rebaudioside A ("Reb A") and Rebaudioside D ("Reb D"). The results at 6, 9, 12, and 24 hours are shown in FIGS. 3B-E, respectively. The results from the reaction without the recombinant AtSUS1 (i.e. a non-coupling reaction) at 12 and 24 hours are shown in FIGS. 3F and 3G, respectively.

FIG. 4A shows the standards of stevioside ("Ste"), Rebaudioside A ("Reb A") and Rebaudioside D ("Reb D"). The result at 20 hours is shown in FIGS. 4B, which includes a rebaudioside Z compound ("Reb Z").

FIG. 5A shows the standards of stevioside ("Ste"), Rebaudioside A ("Reb A") and Rebaudioside D ("Reb D"). The results at 6, 9, 12 and 24 hours are shown in FIGS. 5B-E, respectively.

FIG. 8A shows the standards of rebaudioside E ("Reb E"). The result at 24 hours is shown in FIG. 8B, which includes a rebaudioside Z compound ("Reb Z").

FIG. 12A-12B shows the standards of Rebaudioside E ("Reb E"), Rebaudioside D ("Reb D"). The results from the reaction without the recombinant AtSUS1(FIG. 12C) (i.e. a non-coupling reaction) and with recombinant AtSUS1 (FIG. 12D) (i.e. UGT-SUS coupling reaction) at 6 hours are shown respectively.

Figure 1A:
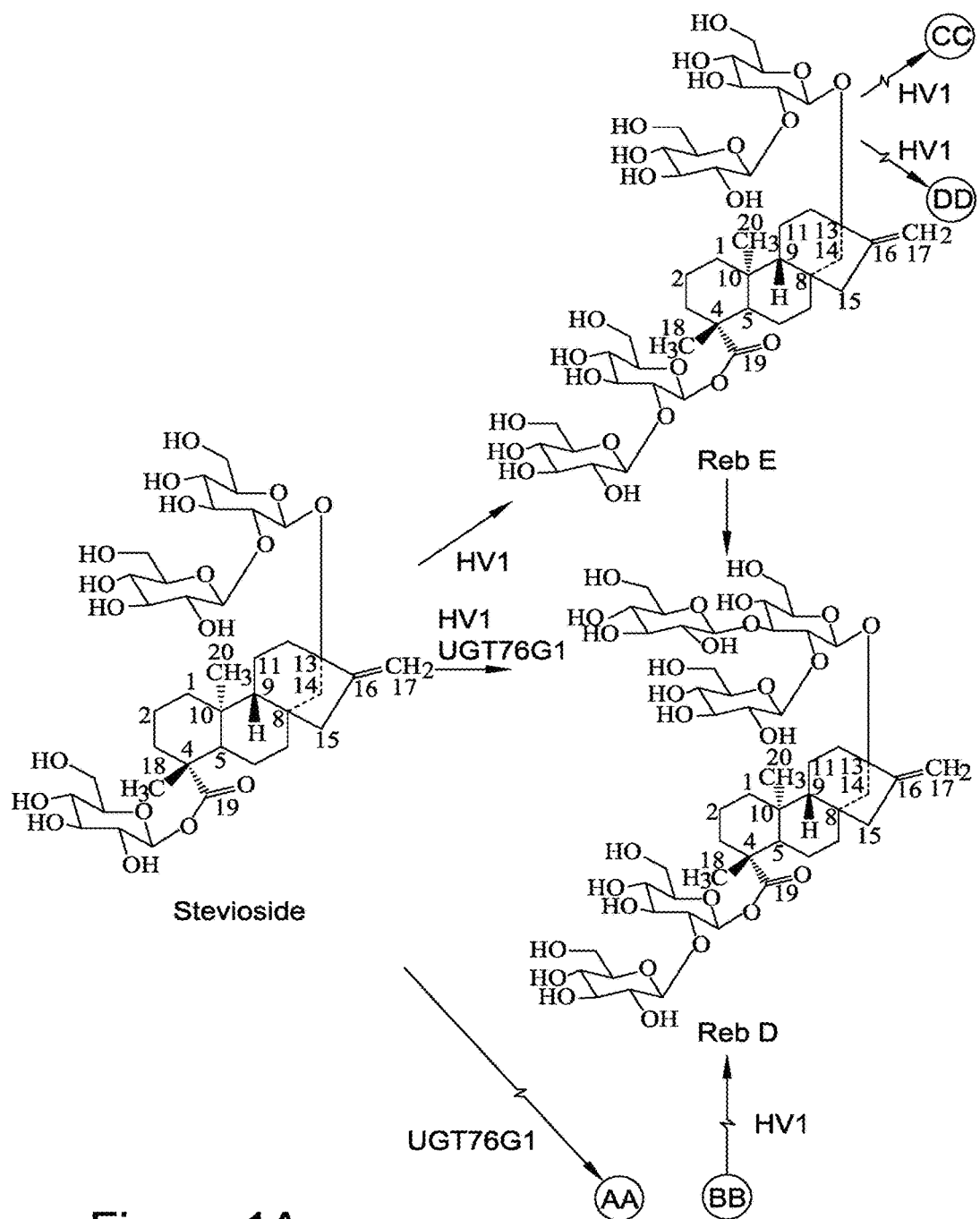
FIGS. 1A-1C depict a scheme illustrating the pathways of steviol glycoside biosynthesis from stevioside. As described herein, the recombinant HV1 polypeptide ("HV1") contains a 1,2-19-O-glucose glycosylation activity which transfers a second sugar moiety to the C-2' of 19-O-glucose of stevioside to produce rebaudioside E ("Reb E"), or similarly to produce rebaudioside D ("Reb D") from rebaudioside A ("Reb A").

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Figure 10:
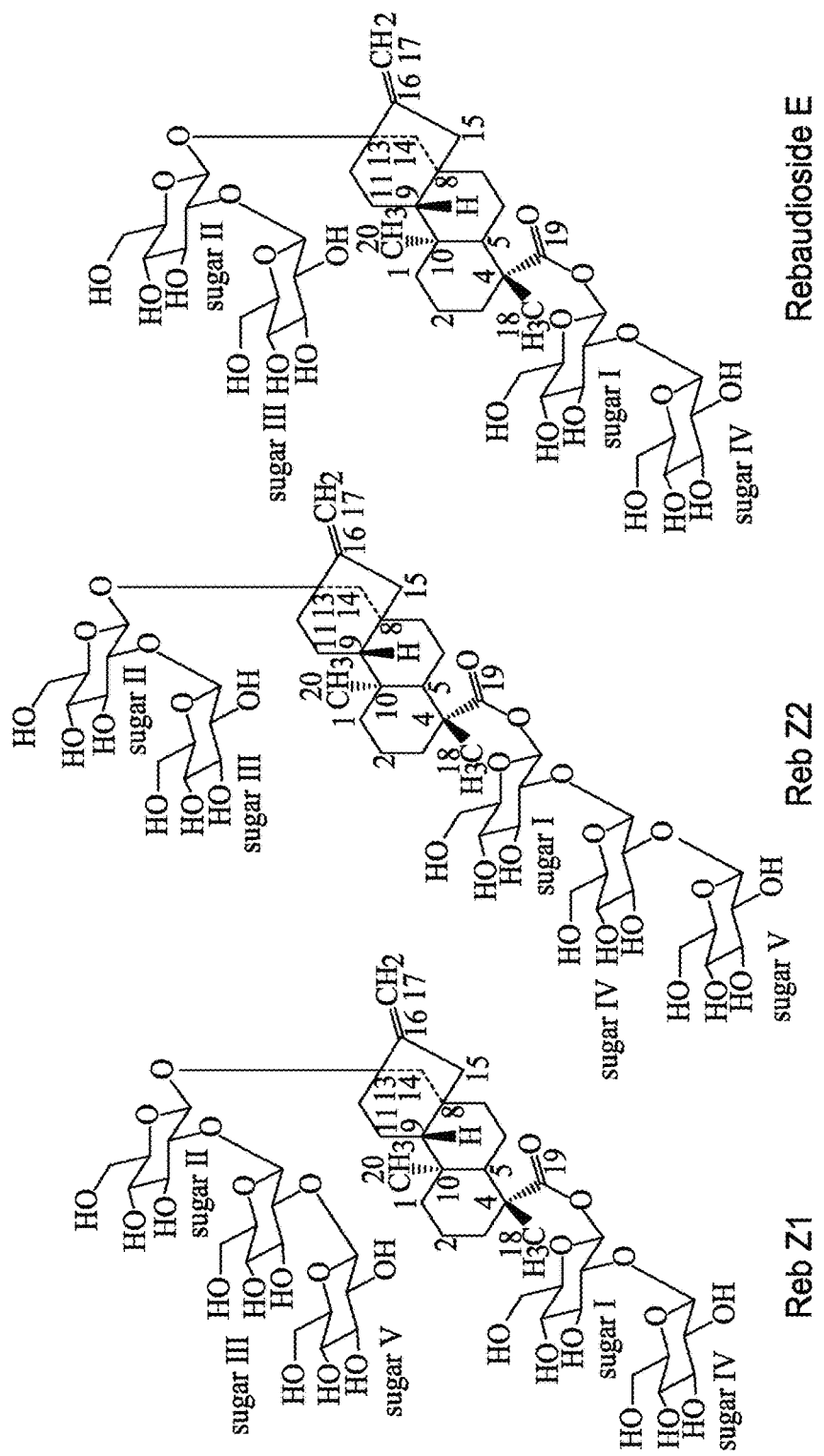
FIG. 10: Structures of Rebaudioside Z (including Reb Z1 and Reb Z2) and Rebaudioside E.

The subject technology provides a recombinant polypeptide that has UDP-glycosyltransferase activities, such as 1,2-19-O-glucose glycosylation activity and 1,2-13-O-glucose glycosylation activity for synthesizing steviol glycosides. The recombinant polypeptide of the subject technology (which can also be referred to as "recombinant HV1 polypeptide" hereinafter) is useful for the biosynthesis of steviol glycoside compounds. In the present disclosure, UDP-glycosyltransferase (UGT) refers to an enzyme that transfers a sugar residue from an activated donor molecule (typically UDP-glucose) to an acceptor molecule. The 1,2-19-O-glucose glycosylation activity refers to an enzymatic activity that transfers a sugar moiety to the C-2' of the 19-O-glucose moiety of stevioside, rebaudioside A or rebaudioside E (FIGS. 1A-1C and FIG. 10). The 1,2-13-O-glucose glycosylation activity refers to an enzymatic activity that transfers a sugar moiety to the C-2' of the 13-O-glucose moiety of rebaudioside E (FIG. 10).

The names of the UGT enzymes used in the present disclosure is consistent with the nomenclature system adopted by the UGT Nomenclature Committee (Mackenzie et al., "The UDP glycosyltransferase gene super family: recommended nomenclature updated based on evolutionary divergence," Pharmacogenetics, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

There is a large UGTs gene family in plants. However, the biological functions of the majority of these UGTs remain unknown.

Definitions

As used herein, the singular forms "a," "an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology is defined as the percentage of amino acid residues in a candidate sequence that are identical with the amino acid residues of a reference polypeptide (such as, for example, SEQ ID NO:6), after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position is a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to as the percentage of identical amino acid residues or nucleotides across the entire length of the shorter of the two sequences.

"Coding sequence" is to be given its ordinary and customary meaning to a person of ordinary skill in the art, and is used without limitation to refer to a DNA sequence that encodes for a specific amino acid sequence.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described, for example, by Sambrook, J., Fritsch, E. F. and Maniatis, T. Molecular Cloning: A Laboratory Manual, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entirety of each of which is hereby incorporated herein by reference.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Recombinant Polypeptides

In one aspect, the present disclosure relates to a recombinant polypeptide having an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99%, and even 100% identity to the amino acid sequence set forth in SEQ ID NO:6. Suitably, the amino acid sequence of the recombinant polypeptide has at least 80% identity to SEQ ID No:6. More suitably, the amino acid sequence of the recombinant polypeptide has at least 85%, at least 90%, at least 91%, at least 92%, at least 93%, at least 94%, at least 95%, at least 96%, at least 97%, at least 98%, at least 99%, and even 100% identity to SEQ ID NO:6. In an exemplary embodiment, the amino acid sequence of the recombinant polypeptide consists of SEQ ID NO:6. Accordingly, the recombinant polypeptide described herein includes functional fragments of SEQ ID NO:6, functional variants of SEQ ID NO:6, and other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:6.

In another aspect, the present disclosure relates to an isolated nucleic acid having a nucleotide sequence encoding the recombinant polypeptide described herein. For example, the isolated nucleic acid can include a nucleotide sequence encoding a polypeptide having an amino acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% identity to the amino acid sequence set forth in SEQ ID NO:6. Suitably, the isolated nucleic acid includes a nucleotide sequence encoding a polypeptide having an amino acid sequence that is at least 80% identity to the amino acid sequence set forth in SEQ ID NO:6. More suitably, the isolated nucleic acid includes a nucleotide sequence encoding a polypeptide having an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:6. The isolated nucleic acid thus includes those encoding functional fragments of SEQ ID NO:6, functional variants of SEQ ID NO:6, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:6.

In an embodiment, the present disclosure relates to an isolated nucleic acid having a nucleotide sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% identity to the nucleotide sequence set forth in SEQ ID NO:7. Suitably, the isolated nucleic acid of includes a nucleotide sequence that has at least 80% identity to the nucleotide sequence set forth in SEQ ID NO:7. More suitably, the isolated nucleic acid includes a nucleotide sequence that has at least 85%, at least 90%, at least 91%, at least 92%, at least 93%, at least 94%, at least 95%, at least 96%, at least 97%, at least 98%, at least 99%, and even 100% identity to the nucleic acid sequence set forth in SEQ ID NO:7.

In another aspect, the subject technology relates to a vector having the nucleic acids described herein, and a host cell having the vector described herein. In some embodiments, the present disclosure relates to an expression vector including at least one polynucleotide of the subject technology and wherein the expression vector, upon transfection into a host cell, is capable of expressing at least one recombinant HV1 polypeptide described herein. In an embodiment, the expression vector includes a nucleotide sequence set forth in SEQ ID NO:7 or a variant thereof.

The design of the expression vector depends on such factors as the choice of the host cell to be transformed, the level of expression of protein desired, and the like. The expression vectors can be introduced into the host cell to thereby produce the recombinant polypeptide of the subject technology, such as the recombinant HV1 polypeptide having an amino acid sequence of SEQ ID NO:6 or a variant thereof.

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

In an embodiment, the expression vectors of the subject technology include bacterial expression vectors, for example recombinant bacteriophage DNA, plasmid DNA or cosmid DNA, yeast expression vectors e.g. recombinant yeast expression vectors, vectors for expression in insect cells, e.g., recombinant virus expression vectors, for example baculovirus, or vectors for expression in plant cells, e.g. recombinant virus expression vectors such as cauliflower mosaic virus (CaMV), tobacco mosaic virus (TMV), or recombinant plasmid expression vectors such as Ti plasmids.

In an embodiment, the vector includes a bacterial expression vector. In another embodiment, the expression vector includes a high-copy-number expression vector; alternatively, the expression vector includes a low-copy-number expression vector, for example, a Mini-F plasmid.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, Nucl. Acid. Res. 18, 6069-6074, (1990), Haun, et al, Biotechniques 13, 515-518 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

In an embodiment, the polynucleotide of SEQ ID NO:7 or a variant thereof is obtained by PCR and introduced into an expression vector using restriction endonuclease digestion and ligation according to techniques that are well known in the art.

The present disclosure further relates to a host cell comprising the expression vector described herein. Suitable hosts of the subject technology typically include microbial hosts or plant hosts. For example, the host cell of the subject technology is selected from the group consisting of bacteria, yeast, filamentous fungi, cyanobacteria algae and plant cell.

The microbial hosts can include any organism capable of expressing the polynucleotide (such as SEQ ID NO:7) to produce the recombinant HV1 polypeptide described herein. Microorganisms useful in the subject technology include bacteria, such as the enteric bacteria (*Escherichia* and *Salmonella* for example) as well as *Bacillus, Acinetobacter, Actinomycetes* such as *Streptomyces, Corynebacterium, Methanotrophs* such as *Methylosinus, Methylomonas, Rhodococcus* and *Pseudomona; Cyanobacteria*, such as *Rhodobacterand Synechocystis*; yeasts, such as *Saccharomyces, Zygosaccharomyces, Kluyveromyces, Candida, Hansenula, Debaryomyces, Mucor, Pichia* and *Torulopsis*; and filamentous fungi such as *Aspergillus* and *Arthrobotrys*, and algae, and *Escherichia, Klebsiella, Pantoea, Salmonella Corynebacterium, Clostridium*, and *Clostridium acetobutylicum*, for example. Preferably, the microbial host is a bacteria (such as *Escherichia*) or a yeast (such as *Saccharomyces*). The expression vectors can be incorporated into these and other microbial hosts to prepare large, commercially useful amounts of steviol glycosides.

In an embodiment, the recombinant polypeptide can be expressed in a host cell that is a plant cell. As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multicellular organism capable of photosynthesis, including monocotyledons and dicotyledons. In some embodiments, the plant cell can be an *Arabidopsis* plant cell, a tobacco plant cell, a soybean plant cell, a petunia plant cell, or a cell from another oilseed crop including, but not limited to, a canola plant cell, a rapeseed plant cell, a palm plant cell, a sunflower plant cell, a cotton plant cell, a corn plant cell, a peanut plant cell, a flax plant cell, and a sesame plant cell.

Useful plant hosts can include any plant that supports the production of the recombinant polypeptides of the subject technology. Suitable green plants for use as hosts include, but are not limited to, soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to, commercially significant hosts such as *Spirulina, Haemotacoccus*, and *Dunaliella*. Suitable plants for the method of the subject technology also include biofuel, biomass, and bioenergy crop plants. Exemplary plants include *Arabidopsis thaliana*, rice (*Oryza sativa*), *Hordeum vulgare*, switchgrass (*Panicum vigratum*), *Brachypodium* spp, *Brassica* spp., and *Crambe abyssinica*.

In some embodiments, the present disclosure includes transgenic host cells or hosts that have been transformed with one or more of the vectors disclosed herein.

Alternatively, the hosts cells may be those suitable for biosynthesis production including single cell organisms, microorganisms, multicell organisms, plants, fungi, bacteria, algae, cultivated crops, non-cultivated crops, and/or the like.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran-mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector.

In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell expression systems and expression vectors containing regulatory sequences that direct high level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYC1, HIS3, GAL1, GAL10, ADH1, PGK, PHOS, GAPDH, ADC1, TRP1, URA3, LEU2, ENO, TPI (useful for expression in *Saccharomyces*); AOX1 (useful for expression in Pichia); and lac, trp, $IP_L$, $IP_R$, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. Molecular and App. Gen., 1:483 498 (1982), the entirety of which is hereby incorporated herein to the extent it is consistent herewith), and the promoter of the chlorophyll a/b binding protein. These two promoters are known to be light-induced in plant cells (see, for example, Genetic Engineering of Plants, an Agricultural Perspective, A. Cashmore, Plenum, N.Y. (1983), pages 29 38; Coruzzi, G. et al., The Journal of Biological Chemistry, 258:1399 (1983), and Dunsmuir, P. et al., Journal of Molecular and Applied Genetics, 2:285 (1983), each of which is hereby incorporated herein by reference to the extent they are consistent herewith).

The choice of plasmid vector depends upon the method that will be used to transform host plants. The skilled artisan is well aware of the genetic elements that must be present on the plasmid vector in order to successfully transform, select and propagate host cells containing the chimeric polynucleotide. The skilled artisan will also recognize that different independent transformation events will result in different levels and patterns of expression (Jones et al., EMBO J. 4:2411 2418 (1985); De Almeida et al., Mol. Gen. Genetics 218:78 86 (1989), each of which is hereby incorporated herein by reference to the extent they are consistent herewith), and thus that multiple events must be screened in order to obtain lines displaying the desired expression level and pattern. Such screening may be accomplished by Southern analysis of DNA blots, Northern analysis of mRNA expression, Western analysis of protein expression, or phenotypic analysis.

Introduction of the expression vector of the subject technology into a plant cell can be performed by a variety of methods known to those of ordinary skill in the art including insertion of a nucleic acid sequence of interest into an Agrobacterium rhizogenes Ri or Agrobacterium tumefaciens Ti plasmid, microinjection, electroporation, or direct precipitation. By way of providing an example, in some embodiments, transient expression of a polynucleotide of interest can be performed by agro-infiltration methods. In this regard, a suspension of Agrobacterium tumefaciens containing a polynucleotide of interest can be grown in culture and then injected into a plant by placing the tip of a syringe against the underside of a leaf while gentle counterpressure is applied to the other side of the leaf. The Agrobacterium solution is then injected into the airspaces inside the leaf through stomata. Once inside the leaf, the Agrobacterium transforms the gene of interest to a portion of the plant cells where the gene is then transiently expressed.

As another example, transformation of a plasmid of interest into a plant cell can be performed by particle gun bombardment techniques (i.e., biolistics). In this regard, a suspension of plant embryos can be grown in liquid culture and then bombarded with plasmids or polynucleotides that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

Host cells can be unmodified cells or cell lines, or cell lines that have been genetically modified. In some embodiments, the host cell is a cell line that has been modified to allow for growth under desired conditions, such as at a lower temperature.

Standard recombinant DNA methodologies may be used to obtain a nucleic acid that encodes a recombinant polypeptide described herein, incorporate the nucleic acid into an expression vector, and introduce the vector into a host cell, such as those described in Sambrook, et al. (eds), Molecular Cloning; A Laboratory Manual, Third Edition, Cold Spring Harbor, (2001); and Ausubel, F. M. et al. (eds.) Current Protocols in Molecular Biology, John Wiley & Sons (1995). A nucleic acid encoding a polypeptide may be inserted into an expression vector or vectors such that the nucleic acids are operably linked to transcriptional and translational control sequences (such as a promoter sequence, a transcription termination sequence, etc.). The expression vector and expression control sequences are generally chosen to be compatible with the expression host cell used.

The expression of polypeptide in a host described herein can be further improved by codon-optimization. For example, modifying a less-common codon with a more common codon may affect the half-life of the mRNA or alter its structure by introducing a secondary structure that interferes with translation of the message. All or a portion of a coding region can be optimized. In some cases the desired modulation of expression is achieved by optimizing essentially the entire gene. In other cases, the desired modulation will be achieved by optimizing part of, but not the entire, sequence of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria may include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

In certain embodiments, the codon optimized nucleic acid sequence can express its protein, at a level which is about 110%, about 150%, about 200%, about 250%, about 300%, about 350%, about 400%, about 450%, or about 500%, of that expressed by a nucleic acid sequence that has not been codon optimized.

In addition to the nucleic acid that encodes the recombinant polypeptide of the subject technology, the expression vector of the subject technology may additionally carry regulatory sequences that control the expression of the protein in a host cell, such as promoters, enhancers or other expression control elements that control the transcription or translation of the nucleic acid(s). Such regulatory sequences are known in the art. It will be appreciated by those skilled in the art that the design of the expression vector, including the selection of regulatory sequences may depend on such factors as the choice of the host cell to be transformed, the level of expression of protein desired, etc. In addition, the recombinant expression vectors of the subject technology may carry additional sequences, such as sequences that regulate replication of the vector in host cells (e.g., origins of replication) and selectable marker genes.

Biosynthesis of Steviol Glycosides

As described herein, the recombinant polypeptides of the present technology have UDP-glycosyltransferase activities, including more particularly a 1,2-19-O-glucose glycosylation activity, and are useful for developing biosynthetic methods for preparing steviol glycosides that are typically of low abundance in natural sources, such as rebaudioside D and rebaudioside E. The recombinant polypeptides of the present technology have UDP-glycosyltransferase activities, are useful for developing biosynthetic methods for preparing novel steviol glycosides, such as rebaudioside Z1 and rebaudioside Z2.

Accordingly, in one aspect, the subject technology also relates to a method of producing a steviol glycoside composition, the method including incubating a substrate with a recombinant polypeptide comprising an amino acid sequence having at least 80% identity to SEQ ID NO:6.

The substrate can be any natural or synthetic compound capable of being converted into a steviol glycoside compound in a reaction catalyzed by one or more UDP-glycosyltransferases. For example, the substrate can be natural stevia extract, steviol, steviol-13-O-glucoside, steviol-19-O-glucoside, steviol-1,2-bioside, rubusoside, stevioside, rebaudioside A, rebaudioside G or rebaudioside E. The substrate can be a pure compound or a mixture of different compounds. Preferably, the substrate includes a compound selected from the group consisting of rubusoside, stevioside, rebaudioside A, rebaudioside E and combinations thereof.

The method described herein also provides a coupling reaction system in which the recombinant peptides described herein is allowed to function in combination with one or more additional enzymes to improve the efficiency or modify the outcome of the overall biosynthesis of steviol glycoside compounds. For example, the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction. In another example, the recombinant polypeptide of the subject technology may produce an intermediate steviol glycoside product (e.g., rebaudioside E), which is further converted to another steviol glycoside (e.g. rebaudioside D) in a reaction catalyzed by another UDP-glycosyltransferase, such as UGT76G1. In another example, the recombinant polypeptide of the subject technology may produce an intermediate steviol glycoside product (e.g., rebaudioside E), which is further converted to another steviol glycoside (e.g., rebaudioside Z1 and rebaudioside Z2) in a reaction catalyzed by UDP-glycosyltransferase, such as HV1.

Accordingly, in one embodiment, the method of the subject technology further includes incubating a recombinant sucrose synthase (SUS) with the substrate and the recombinant polypeptide described herein. The recombinant sucrose synthase converts UDP into UDP-glucose using sucrose as a source of glucose. Suitable sucrose synthase includes those derived from Arabidopsis thaliana and Vigna radiate SUS genes, or from any gene that encodes a functional homolog of the sucrose synthase encoded by the Arabidopsis thaliana and Vigna radiate SUS1 sequence, or the functional homologs thereof. Suitable sucrose synthases can be for example, an Arabidopsis sucrose synthase 1; an Arabidopsis sucrose synthase 3; and a Vigna radiate sucrose synthase. A particularly suitable sucrose synthase can be, for example, Arabidopsis sucrose synthase 1. For example, the recombinant SUS of includes an amino acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, or even 100% identity to the amino acid sequence of AtSUS1 set forth in SEQ ID NO:9. Preferably, the recombinant SUS of the subject technology includes an amino acid sequence that has at least 80% identity to the amino acid sequence of AtSUS1 set forth in SEQ ID NO:9.

The recombinant sucrose synthase of the subject technology can be obtained by expressing a nucleic acid having a nucleotide sequence encoding an amino acid sequence of interest (e.g. one that has at least 80% identity to the amino acid sequence set forth in SEQ ID NO:9) in a host cell as described above. For example, a vector including a nucleotide sequence set forth in SEQ ID NO:10 can be introduced into a microbial host (such as E. Coli) by conventional transformation techniques to produce the recombinant sucrose synthase.

In another embodiment, the method of the subject technology further includes incubating a recombinant UDP-glycosyltransferase with the recombinant sucrose synthase, the substrate, and the recombinant polypeptide described herein. The recombinant UDP-glycosyltransferase can catalyze a different glycosylation reaction than the one catalyzed by the recombinant polypeptide of the subject technology. For example, the recombinant UDP-glycosyltransferase can catalyze the reaction that transfers a sugar moiety to C-3' of the C-13-O-glucose of stevioside to produce rebaudioside A (or similarly to produce rebaudioside D from rebaudioside E), while the recombinant polypeptide of the subject technology transfers a second sugar moiety to the C-2' of 19-O-glucose of stevioside to produce rebaudioside E (or similarly to produce rebaudioside D from rebaudioside A).

Suitable UDP-glycosyltransferase includes any UGT known in the art as capable of catalyzing one or more reactions in the biosynthesis of steviol glycoside compounds, such as UGT85C2, UGT74G1, UGT76G1, or the functional homologs thereof. For example, the UDP-glycosyltransferase as described herein can include an amino acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, or even 100% identity to the amino acid sequence of UGT76G1 set forth in SEQ ID NO:11. Preferably, the UDP-glycosyltransferase includes an amino acid sequence that has at least 80% identity to the amino acid sequence of UGT76G1 set forth in SEQ ID NO:11.

The recombinant UDP-glycosyltransferase can be obtained by expressing a nucleic acid having a nucleotide sequence encoding an amino acid sequence of interest (e.g. one that has at least 80% identity to the amino acid sequence set forth in SEQ ID NO:11) in a host cell as described above. For example, a vector including a nucleotide sequence set forth in SEQ ID NO:12 can be introduced into a microbial host (such as E. Coli) by conventional transformation techniques to produce the recombinant UDP-glycosyltransferase of the subject technology.

Both in vitro and in vivo production of steviol glycoside compounds are encompassed by the subject technology.

For example, the incubation can be an in vitro process, where a substrate is allowed to interact with a recombinant polypeptide of the subject technology. Preferably, in an in vitro process, the recombinant polypeptide is purified before being incubated with the substrate. Conventional polypeptide purification techniques, such as centrifugation, cell lysing, and chromatography, are included in the methods of the subject technology. For example, the nucleic acid encoding the recombinant polypeptide of the subject technology may be cloned into an expressing vector with a Histidine tag, such that the expressed recombinant polypeptide can be purified by affinity column chromatography.

The in vitro method of the subject technology includes any buffer system that is suitable for steviol glycoside production using one or more recombinant polypeptides of the subject technology. Typically, the buffer system is an aqueous solution, such as Tris buffer, HEPES buffer, MOPS buffer, phosphate buffer, with a pH of from about 6.0 to about 8.0. More suitably, the pH is from about 6.5 to about 7.5. Even more suitably, the pH is from about 7.0 to about 7.5.

Typically, in the in vitro method of the subject technology, the substrate is present in the buffer at a concentration of from about 0.2 mg/mL to about 5 mg/mL, preferably from about 0.5 mg/mL to about 2 mg/mL, more preferably from about 0.7 mg/mL to about 1.5 mg/mL.

Typically, in the in vitro method of the subject technology, UDP-Glucose is included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM.

Typically, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

Typically, the reaction temperature of the in vitro method is from about 20° C. to about 40° C., suitably from 25° C. to about 37° C., more suitably from 28° C. to about 32° C.

The present disclosure also provides for a steviol glycoside composition produced by the biosynthetic method described herein. The exact nature of the steviol glycoside composition produced using the method described herein, such as types of molecular species and their percentage content in the final product, depends on the substrate used, the incubation conditions, and the enzymatic activities included in the reaction system. For example, when stevioside is used as substrate, the steviol glycoside composition produced can include rebaudioside A, rebaudioside D, rebaudioside E, rebaudioside Z1 and rebaudioside Z2 and combinations thereof.

The subject technology provides a method for converting the predominant steviol glycoside species (i.e. stevioside and rebaudioside A) in the natural *stevia* extract into rebaudioside D and rebaudioside E, which are otherwise of low abundance in the natural extract. Accordingly, the subject technology also provides a method of enriching the content of one or more specific steviol glycosides (such as rebaudioside D and rebaudioside E), the method including incubating a substrate (such as a natural *stevia* extract) with a recombinant polypeptide comprising an amino acid sequence having at least 80% identity to SEQ ID NO:6. For example, when natural *stevia* extract is used as substrate, the steviol glycoside composition produced can be enriched with rebaudioside D and/or rebaudioside E, which are of low abundance in the natural *stevia* extract.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside D produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside Z1, rebaudioside Z2 or a combination thereof) can be included in food products (such as beverages, soft drinks, ice cream, dairy products, confectioneries, cereals, chewing gum, baked goods, etc.), dietary supplements, medical nutrition, as well as pharmaceutical products.

EXAMPLES

Example 1: Selection of Candidate UGT Genes

Phylogenetic and protein BLAST analysis were used to identify 7 candidate genes belonging to the UGT91 subfamily for 1,2-19-O-glucose glycosylation activity (Table 1).

TABLE 1

List of UGT candidate genes

| Name | Description | Accession | Sequence ID |
|---|---|---|---|
| BD1 | PREDICTED: UDP-glycosyltransferase 91C1-like [*Brachypodium distachyon*] | XP_003560664.1 | SEQ ID NO: 1 |
| BD2 | PREDICTED: UDP-glycosyltransferase 91C1-like [*Brachypodium distachyon*] | XP_003560669.1 | SEQ ID NO: 2 |
| BD3 | PREDICTED: LOW QUALITY PROTEIN: UDP-glycosyltransferase 91C1-like [*Brachypodium distachyon*] | XP_003581636.1 | SEQ ID NO: 3 |
| BD4 | PREDICTED: UDP-glycosyltransferase 91C1-like [*Brachypodium distachyon*] | XP_003580515.1 | SEQ ID NO: 4 |
| BD5 | PREDICTED: LOW QUALITY PROTEIN: UDP-glycosyltransferase 91B1-like [*Brachypodium distachyon*] | XP_003559500.1 | SEQ ID NO: 5 |
| HV1 | predicted protein [*Hordeum vulgare* subsp. *vulgare*] | BAJ98242.1 | SEQ ID NO: 6 |
| HV2 | predicted protein [*Hordeum vulgare* subsp. *vulgare*] | BAJ93155.1 | SEQ ID NO: 8 |

Example 2: Enzymatic Activity Screening of Candidate UGT Genes

Full length DNA fragments of all candidate UGT genes were commercially synthesized. Almost all codons of the cDNA were changed to those preferred for *E. coli* (Genscript, N.J.). The synthesized DNA was cloned into a bacterial expression vector pETite N-His SUMO Kan Vector (Lucigen).

Each expression construct was transformed into *E. coli* BL21 (DE3), which was subsequently grown in LB media containing 50 µg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to a equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidozale.

Figure 1B:
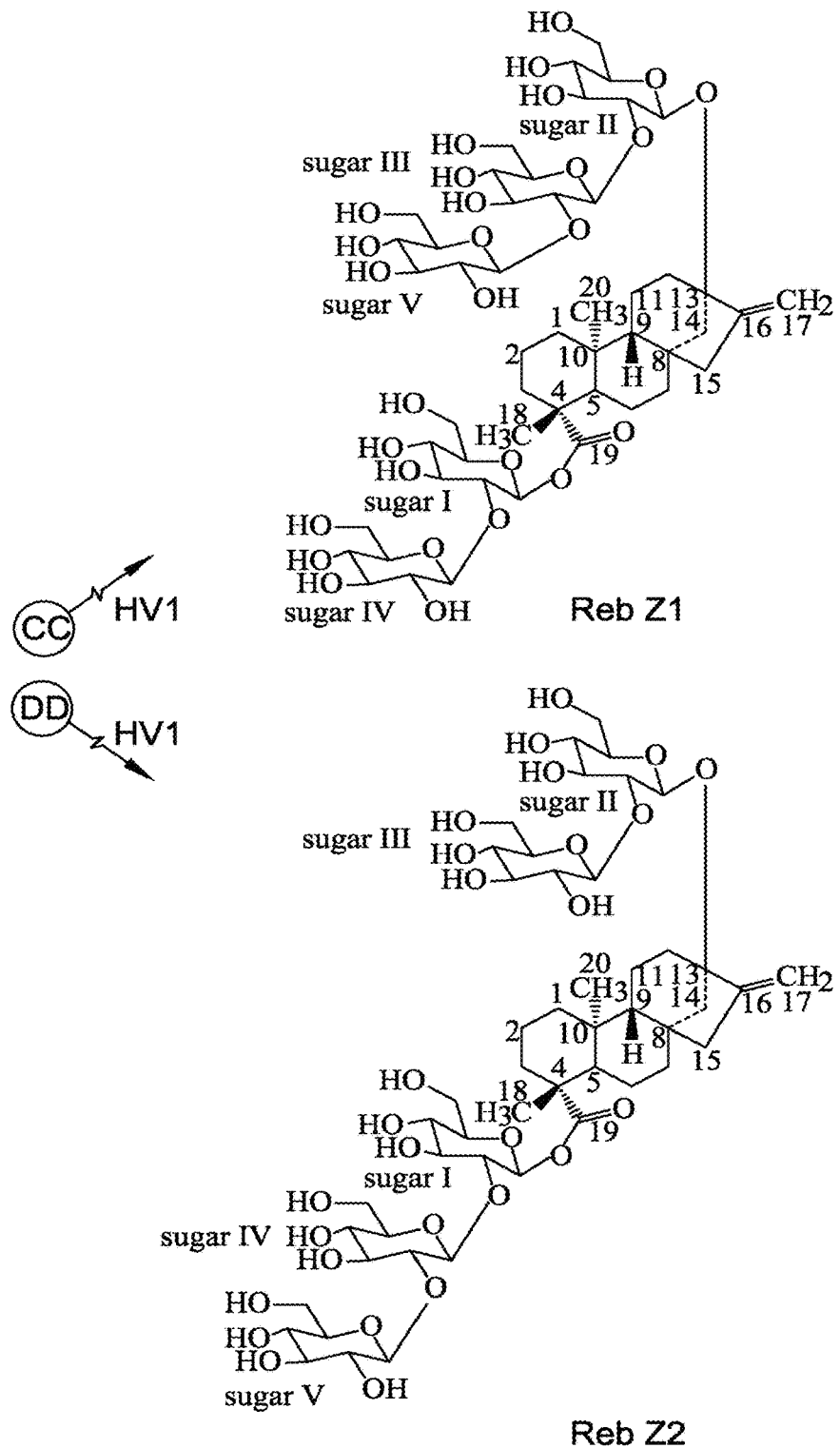
Figure 1C:
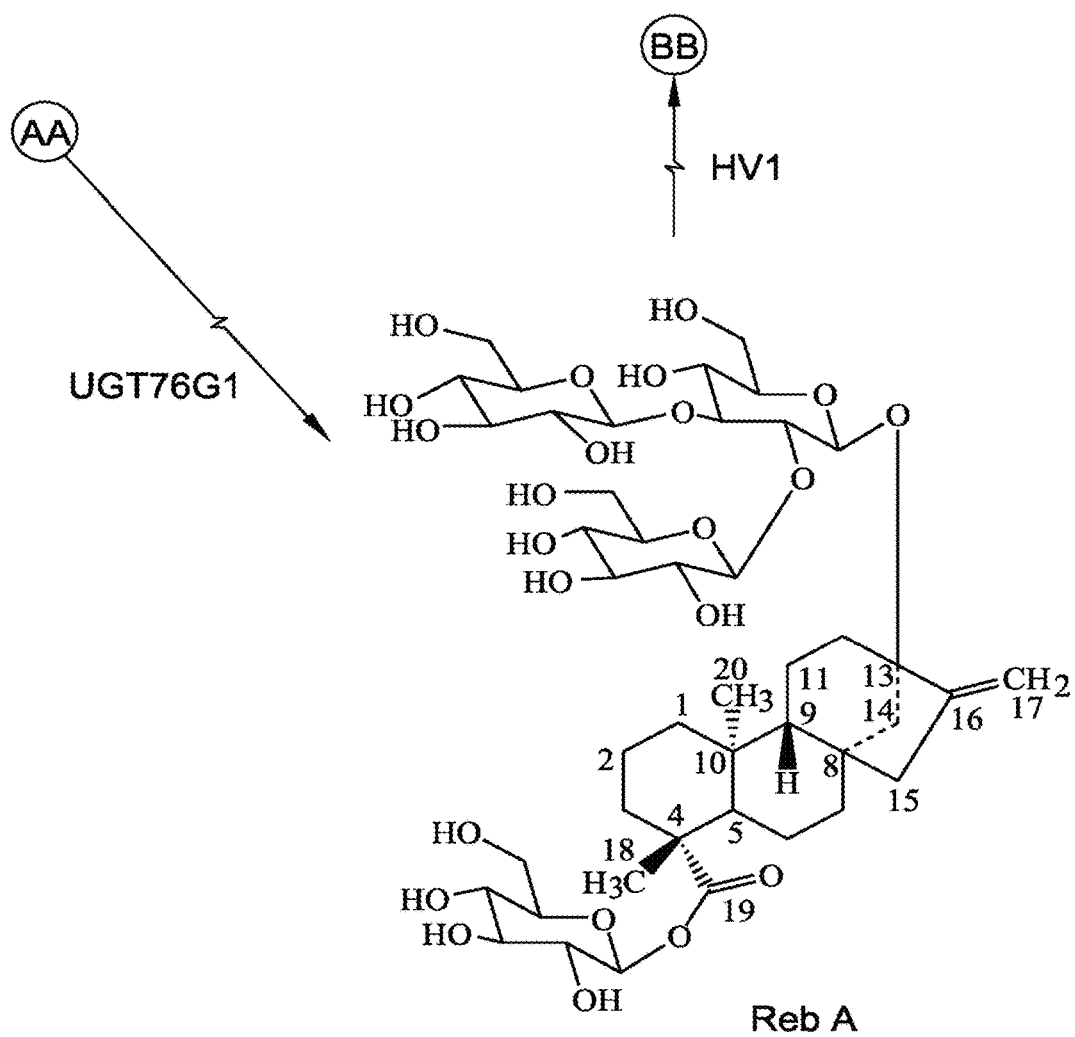

The purified candidate UGT recombinant polypeptides were assayed for 1,2-19-O-glucose glycosylation activity by using stevioside or Reb A as the substrate (FIGS. 1A-1C). Typically, the recombinant polypeptide (10 μg) was tested in a 200 μl in vitro reaction system. The reaction system contains 50 mM potassium phosphate buffer, pH 7.2, 3 mM $MgCl_2$, 1 mg/ml stevioside or rebaudioside A, 1 mM UDP-glucose. The reaction was performed at 30° C. and terminated by adding 200 μL 1-butanol. The samples were extracted three times with 200 μL 1-butanol. The pooled fraction was dried and dissolved in 70 μL 80% methanol for high-performance liquid chromatography (HPLC) analysis. *Stevia* extract (Blue California, Calif.), containing 95% stevioside, was used as stevioside substrate. Rebaudioside A (purity 99%) was also supplied by Blue California.

Figure 2:
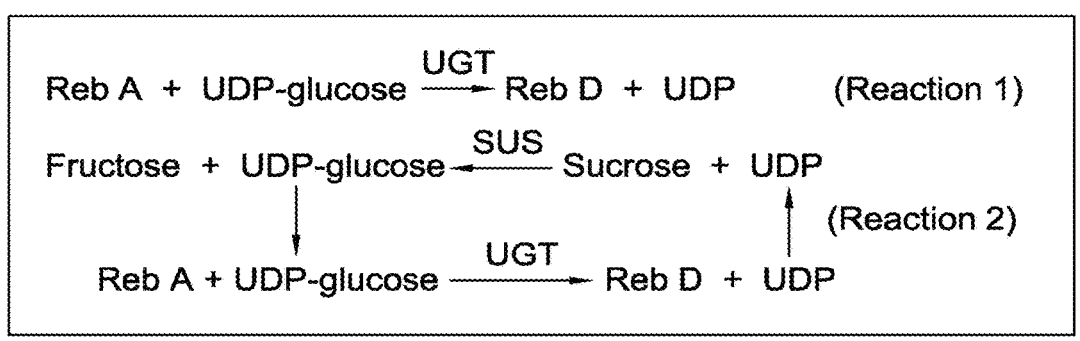
FIG. 2 shows an exemplary scheme of a coupling reaction system of UDP-glycosyltransferase ("UGT") and sucrose synthase ("SUS"). Reaction 1 shows a UGT catalyzed reaction converting rebaudioside A ("Reb A") to rebaudioside D ("Reb D"), which uses UDP-glucose as a glucose donor and results in the production of UDP. Reaction 2 shows a SUS catalyzed reaction converting UDP to UDP-glucose, which uses sucrose as a glucose donor. Reaction 2 also shows that the SUS catalyzed reaction may be coupled to the UGT catalyzed reaction.
Figure 7:
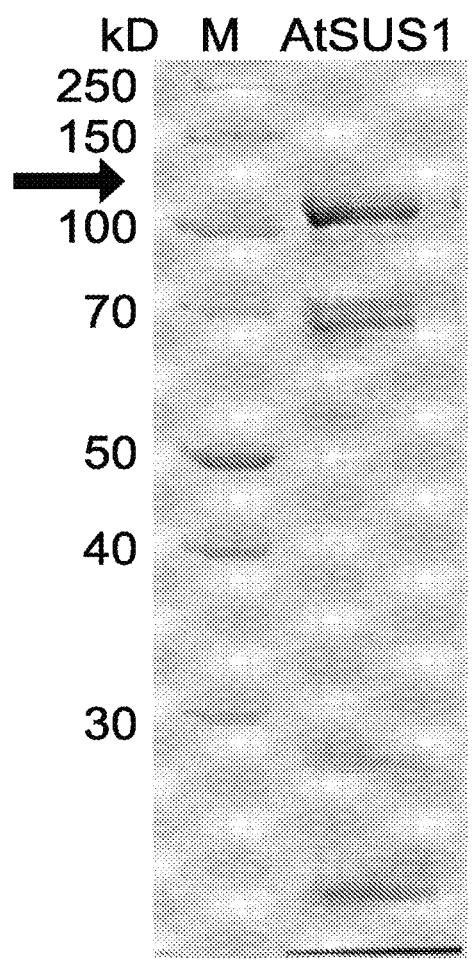
FIG. 7 shows the SDS-PAGE analysis of the purified recombinant AtSUS1 polypeptide.

The UGT catalyzed glycosylation reaction was be coupled to a UDP-glucose generating reaction catalyzed by a sucrose synthase (such as AtSUS1 of SEQ ID NO:9). In this method, the UDP-glucose was generated from sucrose and UDP (FIG. 2), such that the addition of extra UDP-glucose can be omitted. AtSUS1 sequence (Bieniawska et al., Plant J. 2007, 49: 810-828) was synthesized and inserted into a bacterial expression vector. The recombinant AtSUS1 protein was expressed and purified by affinity chromatography. The purified recombinant AtSUS1 polypeptide was analyzed by SDS-PAGE (molecular weight: 106.3 kD, FIG. 7).

Accordingly, the activities of the recombinant UGT polypeptides were tested without AtSUS1 coupling (50 mM potassium phosphate buffer, pH 7.2, 3 mM $MgCl_2$, 1 mg/ml stevioside or rebaudioside A, 1 mM UDP) or with AtSUS coupling (50 mM potassium phosphate buffer, pH 7.2, 3 mM $MgCl_2$, 1 mg/ml stevioside or rebaudioside A, 1 mM UDP and 285 mM sucrose). Typically, 10 μg of AtSUS1 was used for a 200 μl in vitro reaction. The in vitro reaction was incubated at 30° C., and was stopped by extraction using 1-butonal.

HPLC analysis was then performed using a Dionex UPLC ultimate 3000 system (Sunnyvale, Calif.), including a quaternary pump, a temperature controlled column compartment, an auto sampler and a UV absorbance detector. Phenomenex Luna NH2 with guard column was used for the characterization of steviol glycosides. Acetonitrile in water was used for isocratic elution in HPLC analysis. Rebaudioside D, rebaudioside E, rebaudioside Z products were identified by NMR analysis.

Figure 6:
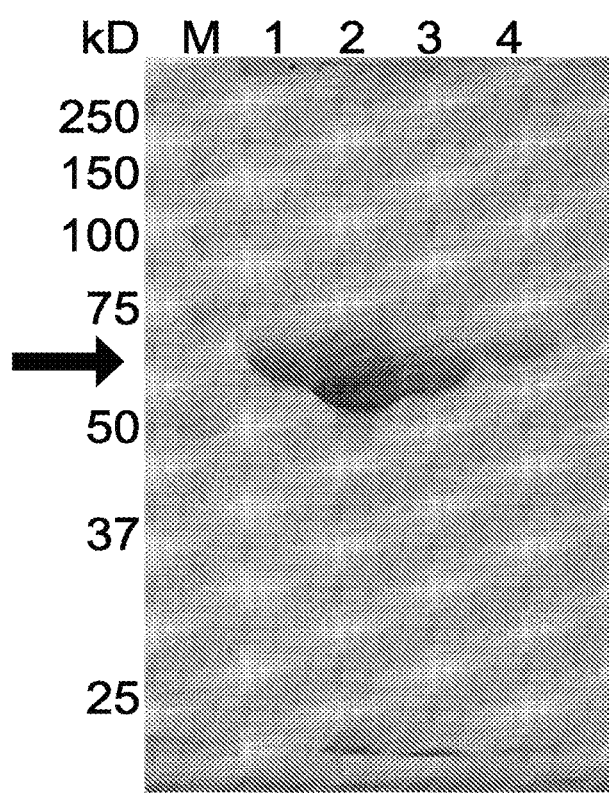
FIG. 6 shows the SDS-PAGE analysis of the purified recombinant HV1 polypeptide.

The recombinant polypeptide (SEQ ID NO:6) encoded by SEQ ID NO:7 showed a 1,2-19-O-glucose glycosylation activity, and was subjected to additional analysis. The gene was derived from *Hordeum vulgare* subsp. *vulgare* (abbreviated as "HV1" herein). The purified recombinant HV1 polypeptide was analyzed by SDS-PAGE (FIG. 6). As shown in FIG. 6, the recombinant HV1 protein (molecular weight: 61.4 kD) was purified by affinity chromatography. The polypeptides encoded by other candidate genes (Table 1) did not show any detectable activity in the assays described herein, even though they share about 62-74% sequence identity with the recombinant HV1 polypeptide.

Figure 3:
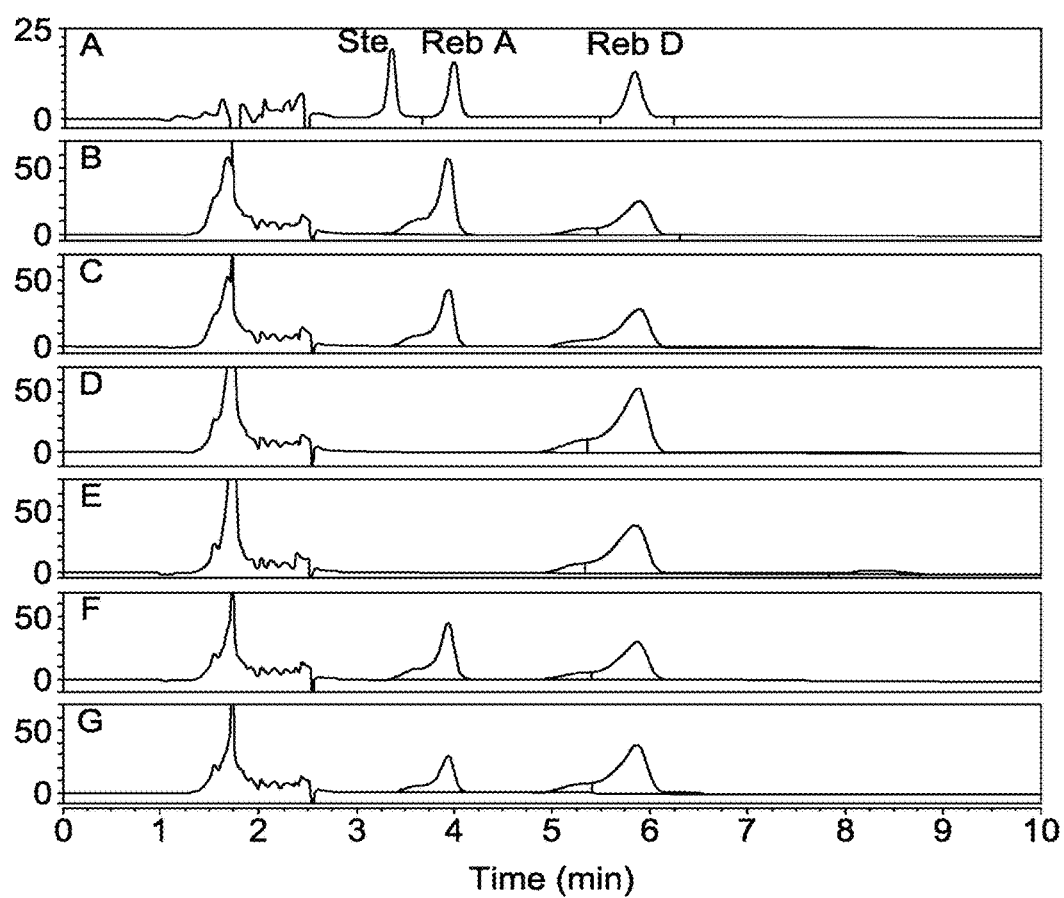
FIG. 3 shows the in vitro production of rebaudioside D ("Reb D") from rebaudioside A ("Reb A") catalyzed by a recombinant HV1 polypeptide (SEQ ID NO:6) and a recombinant AtSUS1 (SEQ ID NO:9) in a HV1-AtSUS1 coupling reaction system as described herein.

As described herein, the recombinant polypeptide of HV1 transferred a sugar moiety to rebaudioside A to produce rebaudioside D in all reaction conditions with or without AtSUS1. Rebaudioside A was completely converted to rebaudioside D by the recombinant HV1 polypeptide in a UGT-SUS coupling reaction system (FIG. 3B-E). However, only partial rebaudioside A was converted to rebaudioside D after 24 hours by the recombinant HV1 polypeptide alone without being coupled to AtSUS1 (FIG. 3F-G). Thus, the recombinant HV1 polypeptide showed a 1,2-19-O-glucose glycosylation activity to produce rebaudioside D from rebaudioside A and AtSUS1 enhanced the conversion efficiency in the UGT-SUS coupling system.

Figure 4:
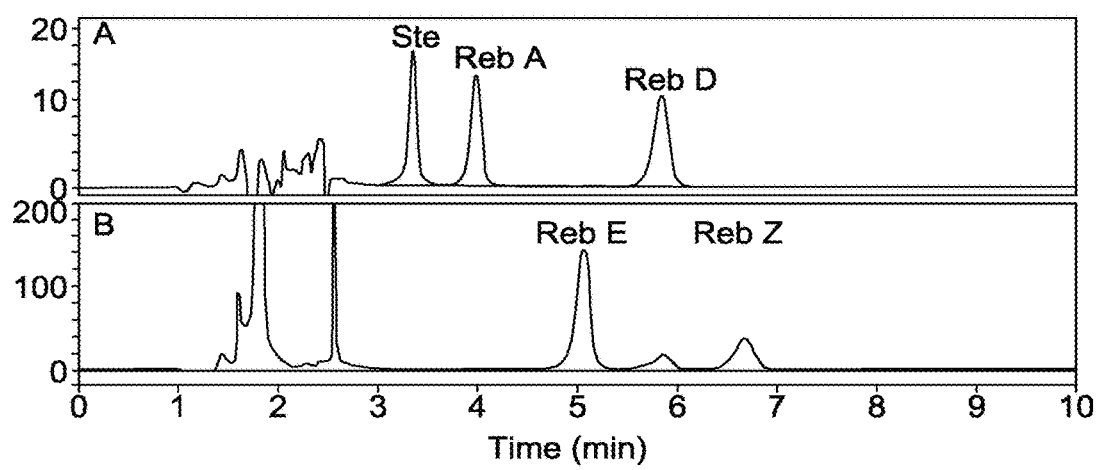
FIG. 4 shows the in vitro production of rebaudioside E ("Reb E") from stevioside catalyzed by a recombinant HV1 polypeptide (SEQ ID NO:6) and a recombinant AtSUS1 (SEQ ID NO:9) in a HV1-AtSUS1 coupling reaction system as described herein.
Figure 8:
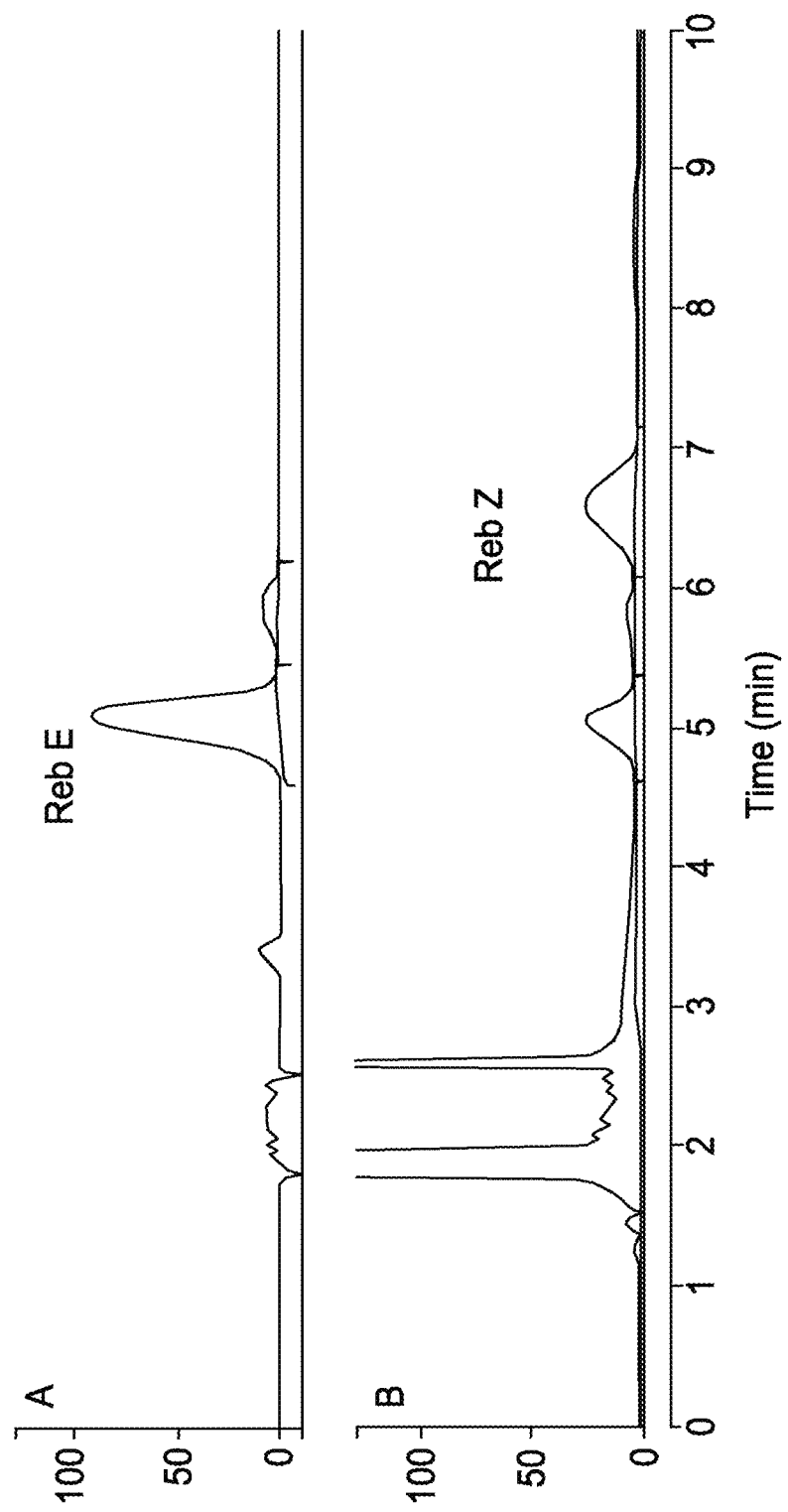
FIG. 8 shows the in vitro production of rebaudioside Z ("Reb Z") from rebaudioside E ("Reb E") catalyzed by a recombinant HV1 polypeptide (SEQ ID NO:6) and a recombinant AtSUS1 (SEQ ID NO:9) in a HV1-AtSUS1 coupling reaction system as described herein.

In addition, the recombinant HV1 polypeptide coupled with AtSUS1 (SEQ ID NO:9) converted stevioside to rebaudioside E in vitro (FIG. 4). An unexpected compound ("Reb Z") having a HPLC retention time 6.68 minute (see, FIG. 4) that was distinctive from rebaudiosides D and E was produced. This compound represents a novel steviol glycoside, and is termed "rebaudioside Z" ("Reb Z"). To confirm the conversion of Reb E to Reb Z, Reb E substrate (0.5 mg/ml) was incubated with the recombinant HV1 polypeptide (20 μg) and AtSUS1 (20 μg) in a UGT-SUS coupling reaction system (200 4) under conditions similar to those used in the examples above. As shown in FIG. 8, Reb Z was produced by the combination of the recombinant HV1 polypeptide and AtSUS1. These results indicated that HV1 can transfer glucose moiety to Reb E to form Reb Z.

Example 3: Steviol glycoside Biosynthesis using the Recombinant HV1 Polypeptide

As shown in FIGS. 1A-1C, rebaudioside D can also be formed by glycosylation of the C-3' of the C-13-O-glucose of rebaudioside E. Thus, rebaudioside D can be produced by different biosynthetic routes (e.g. via rebaudioside A vs. rebaudioside E), depending on the orders in which the glycosylation reactions occur. For example, glycosylation at C-3' of the C-13-O-glucose of stevioside can occur first to produce the intermediate rebaudioside A, followed by glycosylation at C-2' of the 19-O-glucose of rebaudioside A to produce rebaudioside D. So far, UGT76G1 (SEQ ID NO:11) from *stevia* has been identified as an enzyme that transfers a sugar residue to C-3' of the C-13-O-glucose of stevioside to form rebaudioside A.

Figure 9:
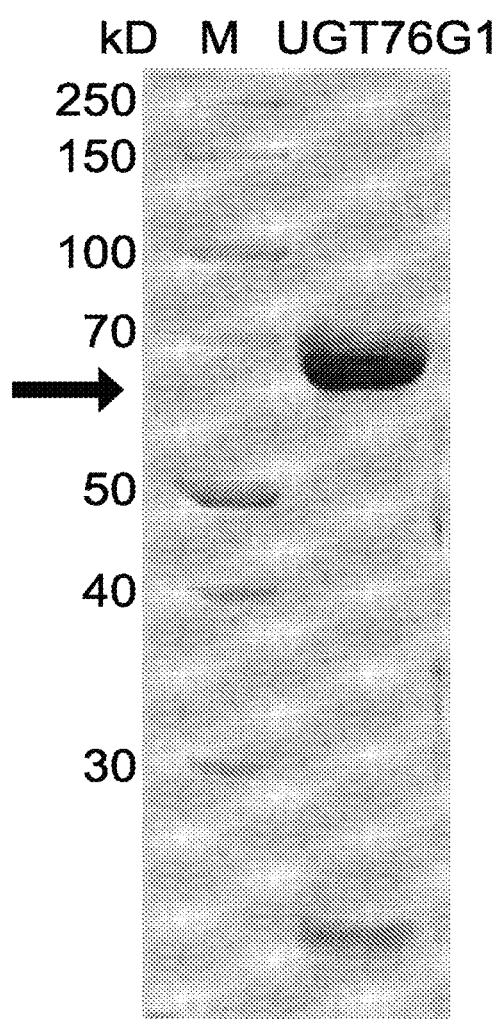
FIG. 9 shows the SDS-PAGE analysis of the purified recombinant UGT76G1 polypeptide.
Figure 12:
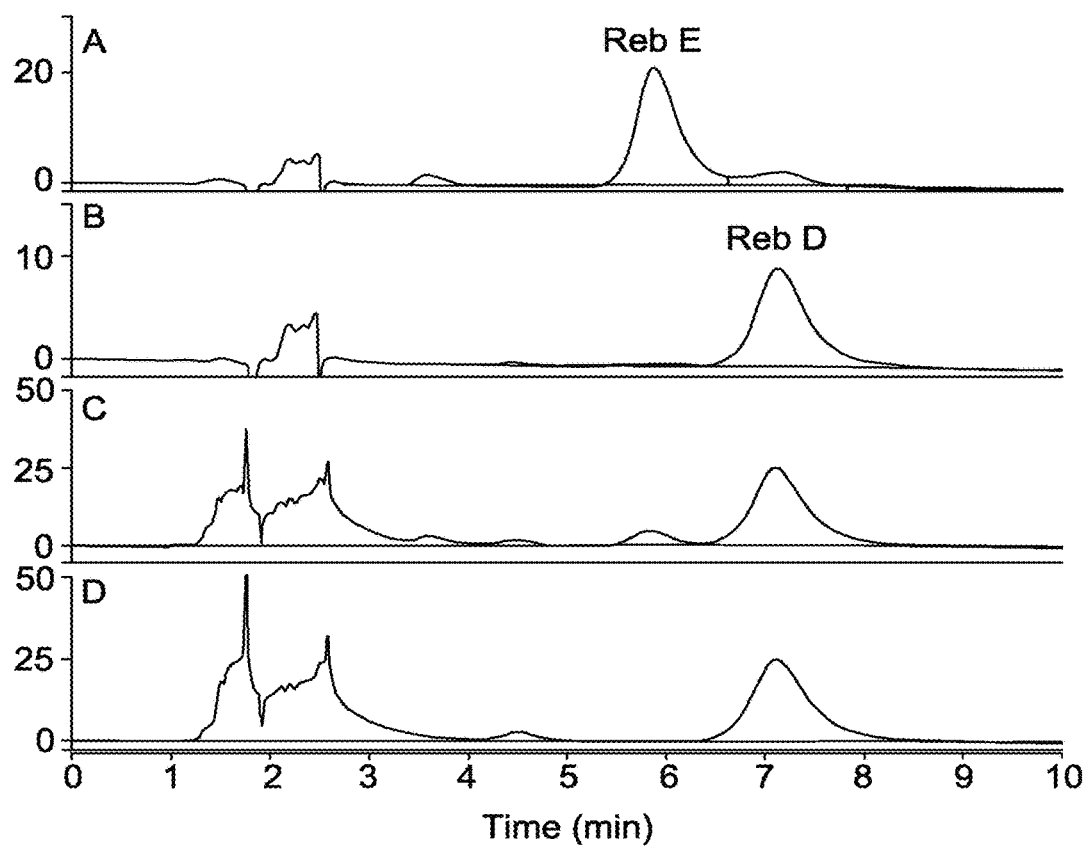
FIG. 12: shows the in vitro production of rebaudioside D ("Reb D") from rebaudioside E ("Reb E") catalyzed by a recombinant UGT76G1 (SEQ ID NO:11).

Codon optimized UGT76G1 cDNA was inserted in a bacterial expression vector, and the recombinant UGT76G1 protein was expressed and purified by affinity chromatography. The purified recombinant UGT76G1 polypeptide was analyzed by SDS-PAGE (molecular weight: 65.4 kD, FIG. 9). The rebaudioside E substrate was incubated with the recombinant UGT76G1, with or without AtSUS1, under conditions similar to those used in the Examples above. The products were analyzed by HPLC. As shown in FIG. 12, rebaudioside D was produced by the recombinant UGT76G1. Addition of recombinant AtSUS in the reaction enhanced the conversion efficiency in UGT-SUS coupling system. Thus, the recombinant UGT76G1 polypeptide showed a 1,3-13-O-glucose glycosylation activity to produce Reb D from Reb E.

Figure 5:
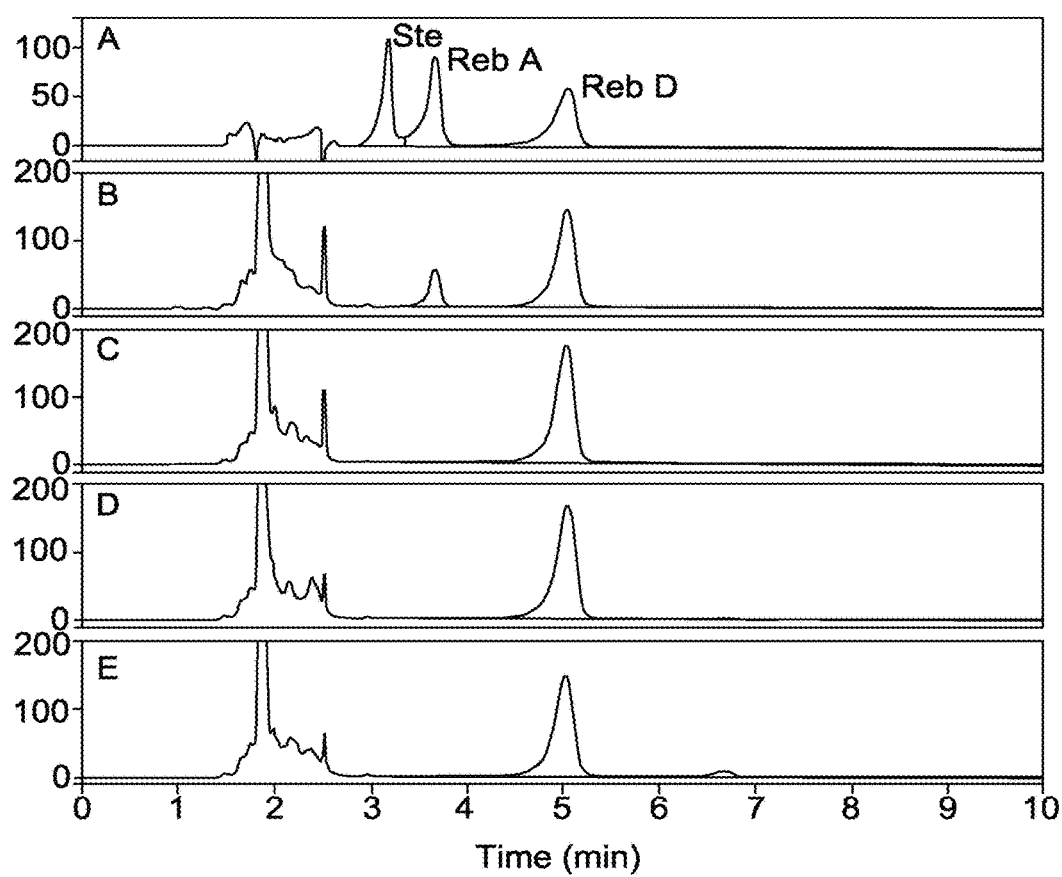
FIG. 5 shows the in vitro production of rebaudioside D ("Reb D") from stevioside catalyzed by a combination of a recombinant HV1 polypeptide (SEQ ID NO:6), a recombinant UGT76G1 (SEQ ID NO:11), and a recombinant AtSUS1 (SEQ ID NO:9).

Accordingly, the catalytic activity of the recombinant HV1 polypeptide for steviol glycoside biosynthesis (e.g., production of rebaudioside D) was further determined in combination with UGT76G1. Stevioside substrate was incubated with the recombinant HV1 polypeptide (10 µg), UGT76G1 (10 µg), and AtSUS1 (10 µg) in a UGT-SUS coupling reaction system (200 µL) under conditions similar to those used in the examples above. The products were analyzed by HPLC. As shown in FIG. 5, rebaudioside D was produced by the combination of the recombinant HV1 polypeptide, UGT76G1, and AtSUS1. Thus, the recombinant HV1 polypeptide, which showed at least a 1,2-19-O-glucose glycosylation activity, can be used in combination with other UGT enzymes (such as UGT76G1) for the complex, multi-step biosynthesis of steviol glycosides.

Example 4: NMR Analysis the Structure of Reb Z

The material used for the characterization of rebaudioside Z (Reb Z) was produced using enzymatic conversion of rebaudioside E and purified by HPLC.

HRMS data were generated with a LTQ Orbitrap Discovery HRMS instrument, with its resolution set to 30 k; scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. The sample was diluted with 2:2:1 acetonitrile:methanol:water (same as infusion eluent) and injected 50 microliters.

NMR spectra were acquired on Bruker Avance DRX 500 MHz or Varian INOVA 600 MHz instrument instruments using standard pulse sequences. The 1D ($^1$H and $^{13}$C) and 2D (COSY, TOCSY, HMQC, and HMBC) NMR spectra were performed in $C_5D_5N$.

Compound Reb Z, shown as a mixture of Reb Z1 and Reb Z2, is shown in FIG. 10. The molecular formula of compound Reb Z has been deduced as $C_{50}H_{80}O_{28}$ on the basis of its positive high resolution (HR) mass spectrum, which showed adduct ions corresponding to [M+Na]$^+$ at m/z 1151.4713; this composition was supported by the $^{13}$C NMR spectral data. The $^1$H NMR spectral data of Reb Z showed the presence of two compounds (Reb Z1 and Reb Z2) in the ratio between 60:40 to 70:30. Hence the $^1$H and $^{13}$C NMR spectral data of Reb Z showed a sets of peaks for each proton and carbon present in its structure. Acid hydrolysis of Reb Z with 5% $H_2SO_4$ afforded D-glucose which was identified by direct comparison with authentic sample by TLC. Enzymatic hydrolysis of Reb Z furnished an aglycone, which was identified as steviol by comparison of $^1$H NMR and co-TLC with standard compound. The $^1$H and $^{13}$C NMR values for compound Reb Z were assigned on the basis of TOCSY, HMQC and HMBC data. The large coupling constants observed for the five anomeric protons of the glucose moieties, suggested their β-orientation as reported for steviol glycosides.

TABLE 2

$^1$H and $^{13}$C NMR spectral data (chemical shifts and coupling constants) for rebaudioside Z ("Reb Z"), and rebaudioside E$^{a-c}$.

| | Reb Z | | Rebaudioside E | |
|---|---|---|---|---|
| Position | $^1$H NMR | $^{13}$C NMR | $^1$H NMR | $^{13}$C NMR |
| 1 | 0.74 t (12.7), 1.65 m | 41.2 | 0.73 t (13.2), 1.68 m | 41.0 |

TABLE 2-continued $^1$H and $^{13}$C NMR spectral data (chemical shifts and coupling constants) for rebaudioside Z ("Reb Z"), and rebaudioside E$^{a-c}$.

| | Reb Z | | Rebaudioside E | |
|---|---|---|---|---|
| Position | $^1$H NMR | $^{13}$C NMR | $^1$H NMR | $^{13}$C NMR |
| 2 | 1.45 m, 2.12 m | 20.6 | 1.46 m, 2.13 m | 20.6 |
| 3 | 1.13 m, 2.922 d (13.2)/2.79 d (12.8) | 38.2 | 1.12 m, 2.78 d (12.8) | 38.2 |
| 4 | — | 44.9/44.8 | — | 44.8 |
| 5 | 0.99 m | 58.1 | 0.97 d (11.8) | 57.9 |
| 6 | 1.87 m, 2.14 m | 22.6 | 1.85 m, 2.09 m | 22.6 |
| 7 | 1.24 m, 1.68 m | 42.2 | 1.27 m, 1.63 m | 42.1 |
| 8 | — | 43.2/43.1 | — | 43.0 |
| 9 | 0.88 br s | 54.5 | 0.88 br s | 54.5 |
| 10 | — | 40.2 | — | 40.2 |
| 11 | 1.68 m | 21.1 | 1.65 m | 21.1 |
| 12 | 1.92 m, 2.28 m | 37.8 | 1.96 m, 2.16 m | 37.8 |
| 13 | — | 86.6 | — | 86.6 |
| 14 | 1.72 m, 2.48 d (10.8) | 44.9/44.8 | 1.74 d (11.4), 2.54 d (11.0) | 44.8 |
| 15 | 1.92 m, 2.14 m | 48.5 | 2.04 m, 2.12 m | 48.5 |
| 16 | — | 155.2/155.0 | — | 154.9 |
| 17 | 5.09/5.12 s, 5.68/5.74 s | 105.4/105.2 | 5.09 s, 5.76 s | 105.4 |
| 18 | 1.43/1.49 s | 29.9 | 1.43 s | 29.8 |
| 19 | — | 176.3/176.1 | — | 176.2 |
| 20 | 1.09 s | 17.3 | 1.10 s | 17.2 |
| 1' | 6.30 d (7.9)/ 6.35 d (7.8) | 93.9/93.6 | 6.30 d (7.9) | 93.9 |
| 2' | 4.38 m | 81.8 | 4.38 m | 81.7 |
| 3' | 4.27 m | 78.5 | 4.26 m | 78.4 |
| 4' | 4.24 m | 71.8 | 4.22 m | 71.8 |
| 5' | 3.94 m | 79.6 | 3.92 m | 79.5 |
| 6' | 4.33 m, 4.46 m | 62.6 | 4.33 m, 4.43 m | 62.6 |
| 1" | 5.12 d (7.4)/ 5.14 d (7.4) | 98.4/98.2 | 5.16 d (7.5) | 98.4 |
| 2" | 4.18 m | 84.9 | 4.17 m | 84.9 |
| 3" | 4.29 m | 78.6 | 4.32 m | 78.5 |
| 4" | 4.20 m | 72.1 | 4.22 m | 72.1 |
| 5" | 3.74 m | 78.5 | 3.72 m | 78.2 |
| 6" | 4.32 m, 4.38 m | 62.8 | 4.26 m, 4.35 m | 62.9 |
| 1''' | 5.33 d (7.8)/ 5.46 d (7.8) | 106.7/104.5 | 5.32 d (7.5) | 107.2 |
| 2''' | 4.14 t (8.4) | 85.7/77.7 | 4.15 t (8.4) | 77.7 |
| 3''' | 4.25 m | 78.7 | 4.26 m | 78.6 |
| 4''' | 4.34 m | 72.1/71.5 | 4.36 m | 72.3 |
| 5''' | 3.88 m | 79.1 | 3.96 m | 79.0 |
| 6''' | 4.43 m, 4.56 m | 63.1 | 4.46 m, 4.56 m | 63.2 |
| 1'''' | 5.48 d (7.9)/ 5.40 d (7.6) | 106.3/104.4 | 5.48 d (7.9) | 106.2 |
| 2'''' | 4.04 t (7.9) | 85.6/77.3 | 4.06 t (7.9) | 76.8 |
| 3'''' | 4.22 m | 78.8 | 4.25 m | 78.7 |
| 4'''' | 4.38 m | 71.4/71.0 | 4.31 m | 71.2 |
| 5'''' | 3.96 m | 79.1 | 4.02 m | 79.1 |
| 6'''' | 4.38 m, 4.57 m | 63.4 | 4.42 m, 4.54 m | 63.4 |
| 1''''' | 5.29 d (7.5)/ 5.34 d (7.5) | 107.1 | | |
| 2''''' | 4.02 m | 77.0 | | |
| 3''''' | 4.21 m | 78.6 | | |
| 4''''' | 4.25 m | 71.6/71.2 | | |
| 5''''' | 3.98 m | 79.1 | | |
| 6''''' | 4.34 m, 4.48 m | 63.3 | | |

$^a$assignments made on the basis of TOCSY, HMQC and HMBC correlations;
$^b$Chemical shift values are in δ (ppm);
$^c$Coupling constants are in Hz.

Based on the results from NMR spectral data and hydrolysis experiments of Reb Z, and a close comparison of the $^1$H and $^{13}$C NMR values of Reb Z with rebaudioside E suggested the mixture of two compounds produced by the enzymatic conversion were deduced as 13-[(2-O-β-D-glucopyranosyl-2-O-β-D-glucopyranosyl-β-D-glucopyranosyl) oxy] ent-kaur-16-en-19-oic acid-2-O-β-D-glucopyranosyl-β-D-glucopyranosyl ester (Reb Z1) or 13-[(2-O-β-D- glucopyranosyl-β-D-glucopyranosyl)oxy] ent-kaur-16-en-19-oic acid-[(2-O-β-D-glucopyranosyl-2-O-β-D-glucopyranosyl-β-D-glucopyranosyl) ester (Reb Z2).

Acid hydrolysis of compound Reb Z. To a solution of compound Reb Z (5 mg) in MeOH (10 ml) was added 3 ml of 5% H$_2$SO$_4$ and the mixture was refluxed for 24 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and CH$_2$Cl$_2$/MeOH/water (10:6:1); the sugars were identified as D-glucose.

Figure 11:
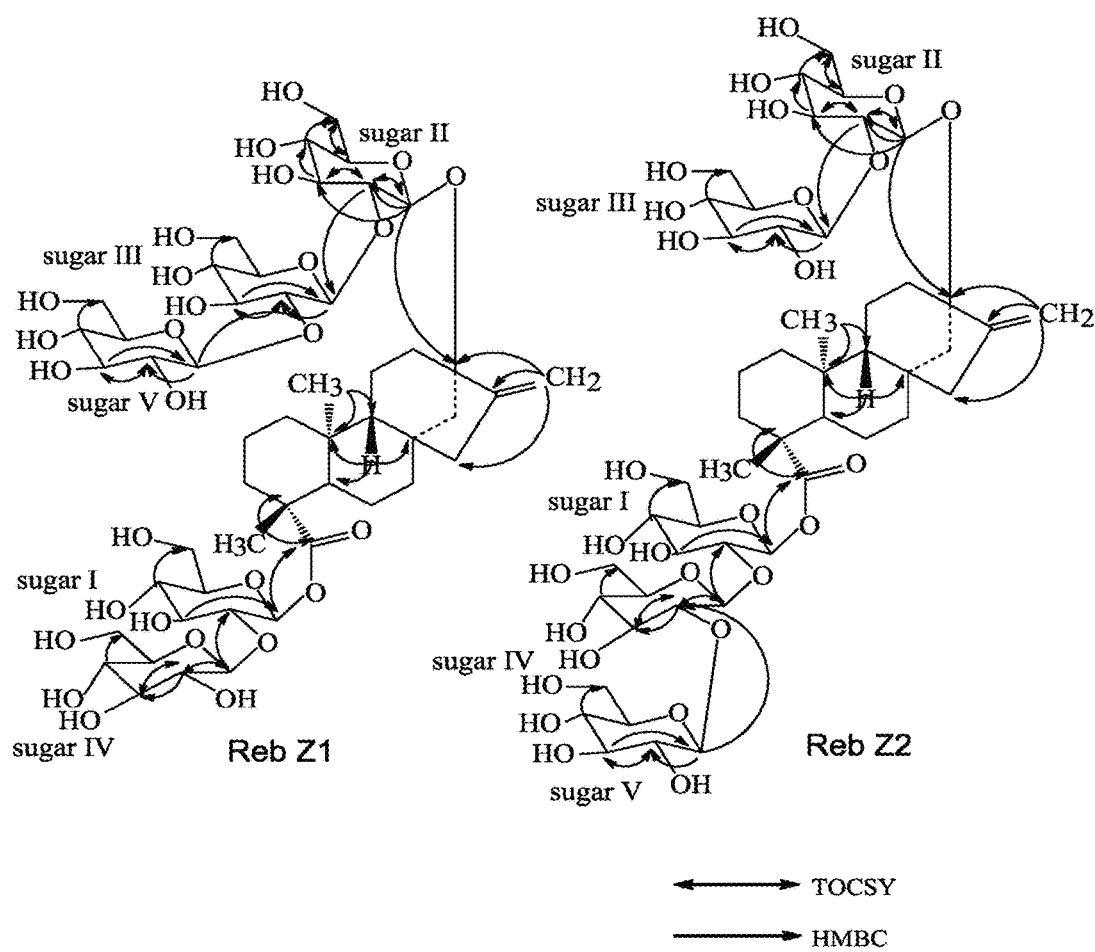
FIG. 11: Key TOCSY and HMBC correlations of Reb Z1 and Reb Z2.

Enzymatic hydrolysis of compound Reb Z. Compound Reb Z (1 mg) was dissolved in 10 ml of 0.1 M sodium acetate buffer, pH 4.5 and crude pectinase from *Aspergillus niger* (50 uL, Sigma-Aldrich, P2736) was added. The mixture was stirred at 50° C. for 96 hr. The product precipitated out during the reaction and was filtered and then crystallized. The resulting product obtained from the hydrolysis of 1 was identified as steviol by comparison of its co-TLC with standard compound and 1H NMR spectral data (FIG. 11).

A mixture of two compounds named Reb Z was produced by the bio-conversion of Rebaudioside E using enzymatic methodology and the structures were characterized as 13-[(2-O-β-D-glucopyranosyl-2-O-β-D-glucopyranosyl-β-D-glucopyranosyl)oxy] ent-kaur-16-en-19-oic acid-2-O-β-D-glucopyranosyl-β-D-glucopyranosyl ester (Reb Z1), or 13-[(2-O-β-D-glucopyranosyl-O-β-D-glucopyranosyl)oxy] ent-kaur-16-en-19-oic acid-[(2-O-β-D-glucopyranosyl-2-O-β-D-glucopyranosyl-β-D-glucopyranosyl) ester (Reb Z2), on the basis of extensive 1D and 2D NMR as well as high resolution mass spectral data and hydrolysis studies.

Thus, the 1,2-19-O-glucose glycosylation activity of the recombinant HV1 polypeptide was confirmed by its ability to transfer a second sugar moiety to the C-2' of a 19-O-glucose of stevioside to produce Rebaudioside E. HV1 recombinant polypeptide also has the activity to transfer the third glucose moiety to the C-2' of a 13-O-glucose or C-2' of a 19-O-glucose of rebaudioside E to produce Reb Z1 or Reb Z2.

What is claimed is:

1. A steviol glycoside composition produced by a method comprising incubating a substrate with a recombinant polypeptide comprising an amino acid sequence having at least 80% identity to SEQ ID NO:6, wherein the steviol glycoside composition comprises rebaudioside Z.

2. The steviol glycoside composition of claim 1, comprising rebaudioside D and rebaudioside Z, rebaudioside E and rebaudioside Z, or rebaudioside D, rebaudioside E and rebaudioside Z.

3. A sweetener comprising the steviol glycoside composition of claim 1.

4. A rebaudioside Z compound produced by a method comprising incubating a substrate with a recombinant polypeptide comprising an amino acid sequence having at least 80% identity to SEQ ID NO:6.

5. The rebaudioside Z compound of claim 4, wherein the rebaudioside Z compound comprises a mixture of rebaudioside Z1 (Reb Z1) and rebaudioside Z2 (Reb Z2).

6. A rebaudioside Z1 compound comprising the structure:

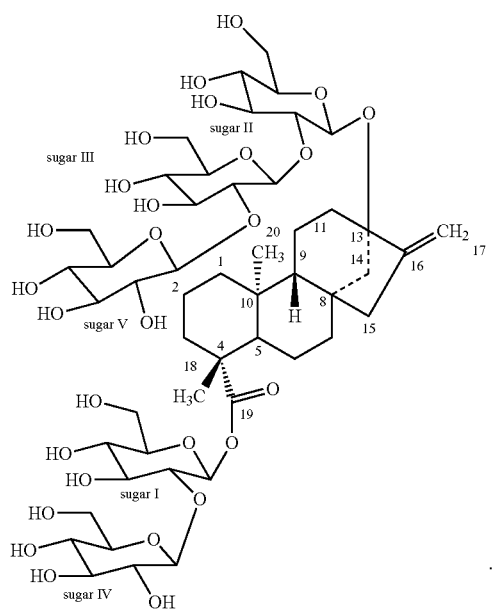

Reb Z1

7. A rebaudioside Z2 compound comprising the structure:

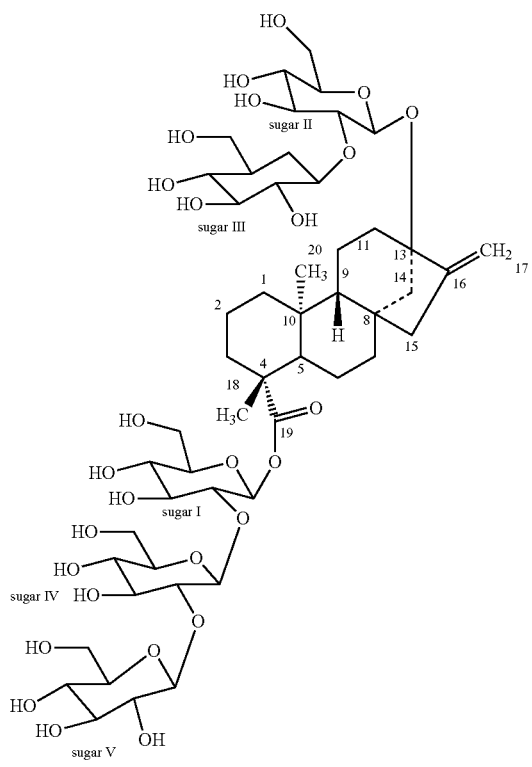

Reb Z2

8. A sweetener comprising a compound having a chemical structure:

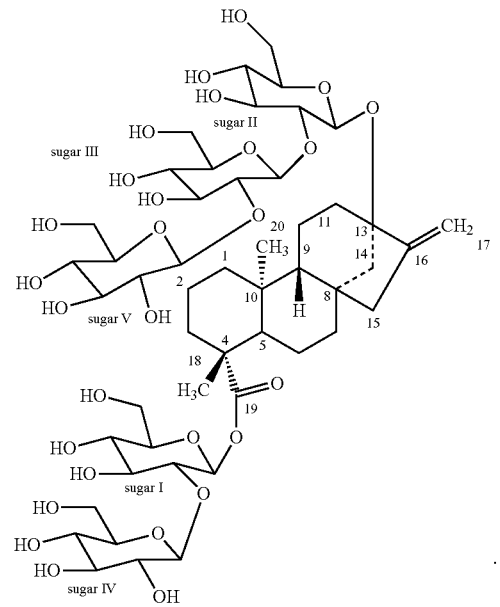

Reb Z1

9. The sweetener of claim 8 further comprising at least one of a filler, a bulking agent and an anticaking agent.

10. A consumable product comprising a sweetening amount of the sweetener of claim 8.

11. The consumable product of claim 10 being selected from the group consisting of beverages, confectioneries, bakery products, cookies, and chewing gums.

12. A sweetener comprising a compound having a chemical structure:

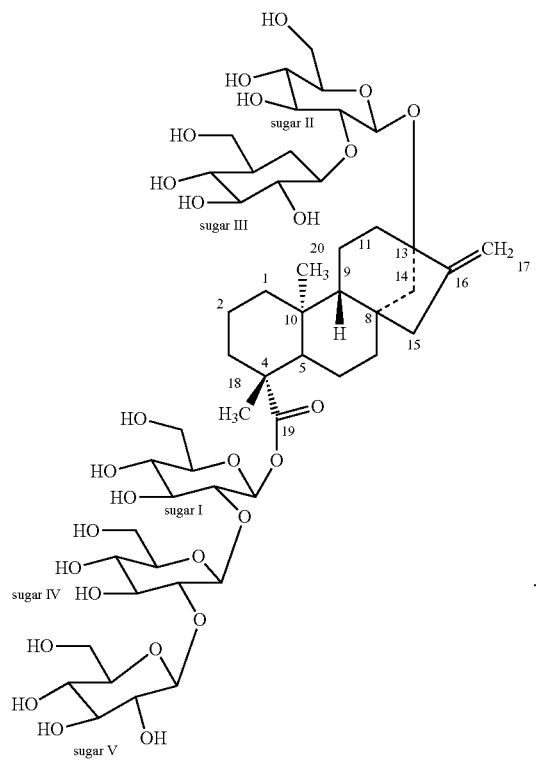

Reb Z2

13. The sweetener of claim 12 further comprising at least one of a filler, a bulking agent and an anticaking agent.

14. A consumable product comprising a sweetening amount of the sweetener of claim 12.

15. The consumable product of claim 14 being selected from the group consisting of beverages, confectioneries, bakery products, cookies, and chewing gums.

* * * * *

SEQUENCE LISTING

```
<160> NUMBER OF SEQ ID NOS: 12

<210> SEQ ID NO 1
<211> LENGTH: 470
<212> TYPE: PRT
<213> ORGANISM: Brachypodium distachyon

<400> SEQUENCE: 1

Met Asp Asp Ala Gly Tyr Ser Ser Ala Tyr Ser Pro Leu His Val Val
1               5                   10                  15

Ile Cys Pro Trp Leu Ala Phe Gly His Gln Leu Pro Cys Leu Asp Leu
            20                  25                  30

Ala Glu Arg Leu Ala Ser Arg Gly His Arg Val Ser Phe Val Ser Thr
        35                  40                  45

Pro Arg Ile Ile Ala Arg Leu Pro Pro Val Arg Pro Thr Ala Ala Gln
    50                  55                  60

Leu Ile Asn Phe Val Ala Leu Pro Leu Pro Ser Val Asp Gly Leu Pro
65                  70                  75                  80

Glu Gly Ala Glu Ser Thr Asn Asp Val Pro Phe Asp Lys Phe Glu Leu
                85                  90                  95

His Arg Lys Ala Phe Asp Gly Leu Ala Leu Pro Phe Ser Glu Phe Leu
            100                 105                 110

Gly Ala Ala Cys Ala Lys Gly Gln Gly His Lys Pro Asp Trp Ile Leu
        115                 120                 125

Val Asp Ile Phe His His Trp Ala Ala Ala Ala Ala Val Glu His Lys
    130                 135                 140

Val Pro Cys Ala Met Leu Leu Leu Gly Ala Ala Ser Phe Ile Ala Ser
145                 150                 155                 160

Gly Ala Gly Gln Leu Phe Glu His Ala Ala Ser Gly Val Gln Val Gln
                165                 170                 175

Glu Arg Pro Ser Ser Thr Glu Pro Pro Lys Phe Glu Ile Glu Met Arg
            180                 185                 190

Glu Leu Ile Ile Thr Gln Arg Ala Ser Gly Met Ser Ile Ala Glu Arg
        195                 200                 205

Val Ser Leu Thr Leu Gln Arg Ser Asn Leu Ala Ala Met Arg Ser Cys
    210                 215                 220
```

```
Val Glu Trp Glu Pro Glu Ser Val Pro Leu Val Ala Ser Leu Gly Val
225                 230                 235                 240

Gly Gly Lys Pro Val Pro Leu Gly Leu Leu Pro Pro Ser Pro Glu
            245                 250                 255

Gly Gly Arg Gly Val Cys Lys Asp Gly Lys Asp Ala Thr Val Lys
            260                 265                 270

Trp Leu Asp Val Gln Pro Ala Lys Ser Val Val Tyr Val Ala Met Gly
            275                 280                 285

Thr Glu Val Pro Leu Pro Ala Glu Gln Val His Glu Leu Ala Phe Gly
            290                 295                 300

Ile Glu Leu Ala Gly Thr Arg Phe Leu Trp Ala Leu Arg Lys Pro Ser
305                 310                 315                 320

Gly Gly Ala Pro Asp Ala Asp Ile Leu Pro Pro Gly Phe Glu Asp Arg
            325                 330                 335

Thr Ala Gly Arg Gly Leu Val Arg Thr Gly Trp Val Pro Gln Met Ser
            340                 345                 350

Ile Leu Gly His Asp Ala Val Gly Ala Phe Leu Thr His Cys Gly Trp
            355                 360                 365

Asn Ser Ile Ile Glu Gly Leu Leu Phe Gly His Pro Leu Val Met Leu
370                 375                 380

Pro Ile Leu Gly Asp Gln Gly Pro Asn Ala Arg Leu Met Glu Gly Lys
385                 390                 395                 400

Lys Val Gly Val Gln Val Gln Arg Asp Gly Asn Asp Gly Ser Phe Asn
            405                 410                 415

Arg Glu Gly Val Ala Met Ala Val Arg Ala Val Met Val Glu Glu Glu
            420                 425                 430

Ser Lys Lys Ile Phe Lys Ala Asn Ala Lys Lys Met Gln Glu Ile Val
            435                 440                 445

Ala Asp Thr Glu Arg His Glu Arg Tyr Ile Asp Gly Phe Ile Gln Gln
            450                 455                 460

Leu Arg Ser Tyr Lys Glu
465                 470

<210> SEQ ID NO 2
<211> LENGTH: 460
<212> TYPE: PRT
<213> ORGANISM: Brachypodium distachyon

<400> SEQUENCE: 2

Met Asp Asn Gly Ser Ser Ser Ser Ser Pro Leu His Val Val
1               5                   10                  15

Ile Cys Pro Trp Leu Ala Phe Gly His Gln Leu Pro Cys Leu Asp Leu
                20                  25                  30

Ala Glu Arg Leu Ala Leu Arg Gly His Arg Val Ser Phe Val Ser Thr
            35                  40                  45

Pro Arg Ile Ile Ala Arg Leu Pro Pro Val Arg Pro Val Ala Ala Ser
        50                  55                  60

Leu Val Asp Leu Val Ala Leu Pro Leu Pro Arg Val Asp Gly Leu Pro
65                  70                  75                  80

Glu Gly Ala Glu Ser Thr Asn Asp Val Pro Tyr Glu Lys Phe Glu Leu
                85                  90                  95

His Arg Lys Ala Phe Asp Gly Leu Ala Val Pro Phe Ser Glu Phe Leu
            100                 105                 110

Arg Ala Ala Cys Ala Glu Glu Gly Lys Lys Pro Asp Trp Ile Ile Val
        115                 120                 125
```

```
Asp Thr Phe His His Trp Ala Ala Ala Ala Ile Glu His Lys Val
            130                 135                 140

Pro Cys Ala Met Leu Met Leu Gly Ala Ala Gly Leu Ile Val Ala Trp
145                 150                 155                 160

Ala Thr Gln Pro Ser Lys His Val Thr Ser Glu Gln Gln Glu Gln Ser
                165                 170                 175

Ala Ala Glu Pro Pro Arg Phe Glu Thr Glu Arg Arg Lys Leu Ala Thr
            180                 185                 190

Thr Gln Arg Ala Ser Gly Met Ser Ile Ala Glu Arg Cys Ser Val Thr
        195                 200                 205

Leu Glu Arg Cys Asn Leu Val Ala Met Arg Ser Cys Leu Glu Trp Glu
210                 215                 220

Pro Glu Ser Ile Pro Leu Ala Thr Thr Ile Gly Gly Lys Gln Leu Val
225                 230                 235                 240

Pro Leu Gly Leu Leu Pro Ser Pro Glu Gly Arg Gly Val Ser
                245                 250                 255

Lys Glu Asp Ala Thr Val Arg Trp Leu Asp Ala Gln Pro Thr Lys Ser
            260                 265                 270

Val Val Tyr Val Ala Leu Gly Ser Glu Val Pro Leu Gly Ala Lys Glu
        275                 280                 285

Val His Glu Leu Ala Leu Gly Leu Glu Leu Ala Gly Thr Arg Phe Leu
290                 295                 300

Trp Ser Leu Arg Lys Pro Ser Gly Val Ser Asp Ala Asp Ile Leu Pro
305                 310                 315                 320

Ser Gly Phe Glu Glu Arg Thr Arg Gly Arg Gly Leu Val Thr Met Gly
                325                 330                 335

Trp Val Pro Gln Ile Ser Val Leu Ala His Gly Ala Val Gly Ala Phe
            340                 345                 350

Leu Thr His Cys Gly Trp Asn Ser Ile Ile Glu Gly Leu Gln Phe Gly
        355                 360                 365

His Pro Leu Val Met Leu Pro Ile Phe Gly Asp Gln Gly Pro Asn Ala
370                 375                 380

Arg Met Met Glu Gly Arg Lys Val Gly Val Gln Val Pro Arg Asp Glu
385                 390                 395                 400

Ser Asn Gly Ser Phe Asp Arg Glu Gly Val Ala Thr Thr Val Arg Ala
                405                 410                 415

Val Ala Val Glu Glu Glu Gly Asn Arg Ile Phe Thr Ala Asn Ala Lys
            420                 425                 430

Lys Met Gln Glu Ile Val Ala Asp Lys Gly Cys His Asp Lys Tyr Val
        435                 440                 445

Asp Lys Phe Ile Gln Lys Leu Arg Ser Tyr Met Glu
450                 455                 460

<210> SEQ ID NO 3
<211> LENGTH: 466
<212> TYPE: PRT
<213> ORGANISM: Brachypodium distachyon
<220> FEATURE:
<221> NAME/KEY: MISC_FEATURE
<222> LOCATION: (407)..(407)
<223> OTHER INFORMATION: Unknown

<400> SEQUENCE: 3

Met Asp Ala Ala Gly Ser Ser Ser Ser Ser Pro Leu Arg Ile Ala Ile
1               5                   10                  15
```

```
Val Pro Trp Leu Ala Phe Gly His Leu Leu Pro Tyr Leu Glu Leu Ala
            20                  25                  30

Glu Arg Leu Ala Ala Arg Gly His Arg Val Ser Phe Val Ser Thr Pro
        35                  40                  45

Arg Asn Leu Ala Arg Leu Pro Pro Leu Arg Pro Ala Ala Ala Pro Arg
    50                  55                  60

Val Asp Leu Val Ala Leu Pro Leu Pro Arg Val Glu Gly Leu Pro Asp
65                  70                  75                  80

Gly Ala Glu Ser Thr Asn Asp Val Pro Asp Asp Glu Arg Glu Pro Leu
                85                  90                  95

Trp Lys Ala Phe Asp Gly Leu Ala Ala Pro Phe Ala Gly Phe Leu Thr
            100                 105                 110

Ala Ala Cys Ala Asp Glu Gly Thr Arg Pro His Trp Ile Ile Ala Asp
        115                 120                 125

Ser Phe His His Trp Ala Ala Ala Ala Leu Glu His Lys Val Pro
    130                 135                 140

Cys Ala Met Leu Leu Pro Thr Ala Ala Leu Ile Ala Ala Ser Ala Gly
145                 150                 155                 160

Ala Gly Arg Pro Ser Pro Glu Glu His Ala Glu Gln Gln Pro Gln Pro
                165                 170                 175

Arg Tyr Glu Gln Glu Gly Arg Ala Thr Leu Leu Thr Asp Gly Asp Met
            180                 185                 190

Ser Gly Met Ser Ile Met Gln Arg Ser Val Leu Thr Leu Glu Arg Cys
        195                 200                 205

Lys Leu Thr Ala Ile Arg Ser Cys Val Glu Trp Glu Pro Glu Cys Leu
    210                 215                 220

Pro Leu Val Ser Glu Phe Ile Gly Lys Pro Val Val Pro Leu Gly Leu
225                 230                 235                 240

Leu Pro Pro Ser Pro Asp Gly Gly Arg Arg Ala Ala Asn Thr Asn Gly
                245                 250                 255

Glu Asp Ala Thr Ile Arg Trp Leu Asp Ala Gln Pro Pro Asn Ser Val
            260                 265                 270

Val Tyr Val Ala Leu Gly Ser Glu Val Pro Leu Pro Val Glu Gln Thr
        275                 280                 285

His Glu Leu Ala Leu Gly Leu Glu Leu Ser Lys Thr Arg Phe Leu Trp
    290                 295                 300

Ala Leu Arg Lys Pro Ser Gly Val Leu Asp Ala Glu Met Leu Pro Met
305                 310                 315                 320

Gly Phe Gln Glu Arg Ile His Gly His Gly Leu Val Thr Thr Gly Trp
                325                 330                 335

Val Pro Gln Met Ser Ile Leu Ala His Gly Ala Val Gly Ser Phe Leu
            340                 345                 350

Thr His Cys Gly Arg Asn Ser Leu Ile Glu Gly Leu Leu Phe Gly His
        355                 360                 365

Pro Leu Ile Met Leu Pro Ile Phe Gly Asp Gln Gly Pro Asn Ala Arg
    370                 375                 380

Leu Met Glu Gly Lys Lys Val Gly Leu Gln Val Ala Arg Asn Glu Asn
385                 390                 395                 400

Asp Gly Ser Phe Asp Arg Xaa Gly Val Ala Ser Ala Val Arg Ser Val
                405                 410                 415

Met Leu Glu Glu Asp Ala Arg Lys Ser Phe Val Ala Asn Ala Leu Glu
            420                 425                 430

Met Gln Lys Ile Val Ala Asp Lys Glu Arg His Glu Arg Tyr Ile Asp
```

```
              435                 440                 445
Glu Phe Ile His Gln Leu Arg Ser Tyr Thr Ser Ala Pro Thr Ser Asp
    450                 455                 460

Arg Asn
465

<210> SEQ ID NO 4
<211> LENGTH: 460
<212> TYPE: PRT
<213> ORGANISM: Brachypodium distachyon

<400> SEQUENCE: 4

Met Asp Ala Ala Gly Ser Ser Pro Pro Leu Arg Ile Val Ile Val Pro
1               5                   10                  15

Trp Leu Ala Phe Gly His Met Leu Pro Tyr Leu Glu Leu Ala Glu Arg
            20                  25                  30

Leu Ala Ala Arg Gly His Arg Val Ser Tyr Val Ser Thr Pro Arg Asn
        35                  40                  45

Leu Ala Arg Leu Pro Pro Leu Arg Pro Ala Ala Pro Arg Val Asp
    50                  55                  60

Leu Val Ala Leu Pro Leu Pro Arg Val Glu Gly Leu Pro Asp Gly Ala
65                  70                  75                  80

Glu Ser Thr Asn Asp Val Pro Asp Glu Arg Glu Pro Leu Trp Lys
                85                  90                  95

Ala Phe Asp Gly Leu Ala Ala Pro Phe Arg Ser Val Pro Arg Gln Arg
            100                 105                 110

Cys Ala Arg Asp Asp Thr Arg Pro His Trp Ile Leu Ala Asp Cys Phe
        115                 120                 125

His His Trp Ala Val Asp Ala Ala Leu Asp His Lys Val Pro Cys Ala
    130                 135                 140

Met Phe Leu Pro Thr Ala Ala Val Ile Ala Thr Met Pro Gln Arg Gln
145                 150                 155                 160

Pro Asp His Ala Ala Ser Ala Pro Ala Glu His Ala Val Pro Arg His
                165                 170                 175

Glu Ile Glu Ala Thr Ala Pro Leu Leu Ser Asp Gln Gly Val Ser Gly
            180                 185                 190

Met Ser Ile Val Gln Arg Tyr Leu Leu Thr Lys Glu Arg Cys Thr Val
        195                 200                 205

Gly Ala Ile Arg Ser Cys Val Glu Trp Glu Pro Asp Ser Tyr Pro Leu
    210                 215                 220

Ala Ala Thr Ile Leu Gly Met Pro Val Val Pro Leu Gly Leu Leu Pro
225                 230                 235                 240

Pro Ser Pro Asp Gly Gly Arg Arg Ala Pro Asp Gly Ser Glu His Ala
                245                 250                 255

Thr Val Arg Trp Leu Asp Ala Gln Pro Pro Ser Ser Val Val Tyr Val
            260                 265                 270

Ala Leu Gly Ser Glu Val Pro Leu Pro Val Asp His Val His Glu Leu
        275                 280                 285

Ala Leu Gly Leu Glu Leu Ala Gly Thr Arg Phe Leu Trp Ala Leu Arg
    290                 295                 300

Lys Pro Asn Gly Val Pro Asp Ala Asp Met Leu Pro Ala Gly Phe Gln
305                 310                 315                 320

Asp Arg Thr Arg Gly His Gly Leu Val Thr Thr Gly Trp Val Pro Gln
                325                 330                 335
```

```
Met Ser Ile Leu Ala His Gly Ala Val Gly Ala Phe Leu Thr His Cys
                340                 345                 350

Gly Arg Asn Ser Leu Ile Glu Gly Leu Leu Gly His Pro Leu Val
            355                 360                 365

Met Leu Pro Ile Phe Gly Asp Gln Gly Pro Asn Ala Arg Ala Met Glu
    370                 375                 380

Arg Lys Lys Val Gly Leu Gln Val Lys Arg Asp Asp Asn Asp Gly Ser
385                 390                 395                 400

Phe Asn Arg Glu Gly Val Ala Asp Ala Val Arg Gly Val Met Val Asp
                405                 410                 415

Gly Glu Ala Arg Arg Gly Phe Val Ala Asn Ala Arg Lys Met Gln Asn
            420                 425                 430

Val Val Ala Asp Glu Glu Leu Gln Glu Arg Tyr Val Asp Gly Phe Val
            435                 440                 445

Gln Glu Leu Arg Ser Tyr Thr Thr Ala Ala Ser Glu
            450                 455                 460

<210> SEQ ID NO 5
<211> LENGTH: 471
<212> TYPE: PRT
<213> ORGANISM: Brachypodium distachyon
<220> FEATURE:
<221> NAME/KEY: MISC_FEATURE
<222> LOCATION: (323)..(323)
<223> OTHER INFORMATION: Unknown

<400> SEQUENCE: 5

Met Asp Asp Gly Ser Ser Ser Pro Leu His Val Val Ile Cys Pro
1               5                   10                  15

Trp Leu Ala Phe Gly His Leu Leu Pro Cys Leu Asp Leu Ala Gln Cys
                20                  25                  30

Leu Ala Ser Arg Gly His Arg Val Ser Phe Val Ser Thr Pro Cys Asn
            35                  40                  45

Ile Ala Cys Leu Leu Val Pro Pro Ala Met Ala Pro Leu Val Asp
    50                  55                  60

Phe Val Glu Leu Pro Phe Pro Phe Pro His Val Asp Gly Leu Ser Glu
65                  70                  75                  80

Arg Lys Leu His Ile Pro Pro Ile Gly Asp Lys Phe Glu Leu His
                85                  90                  95

Arg Lys Ala Phe Asp Gly Leu Ala Met Pro Phe Ser Glu Leu Leu Gly
            100                 105                 110

Ala Ser Cys Ala Glu Gly Gly Lys Lys Leu Asp Trp Val Ile Val Asp
            115                 120                 125

Ile Phe His His Trp Ala Ala Ala Asp Thr Leu Glu Tyr Lys Val Pro
    130                 135                 140

Ile Gly Ala Ala Asn Val Ile Ala Thr Trp His Gly Arg Leu Val Lys
145                 150                 155                 160

His Thr Thr Met Ser Lys Gln Glu Gln Pro Ala Ser Lys Leu Pro Arg
                165                 170                 175

Phe Glu Ile Glu Arg Arg Gln Leu Ser Thr Thr Gln Arg Ala Ser Gly
            180                 185                 190

Met Ser Ile Ala Glu Arg Ile Ser Leu Thr Leu Arg Arg Cys Asn Leu
            195                 200                 205

Val Val Met Arg Thr Arg Leu Glu Trp Glu Pro Glu Ser Val Pro Leu
    210                 215                 220

Ala Ala Ser Leu Gly Gly Lys Pro Val Ile Ser Leu Gly Leu Leu Pro
```

```
                225                 230                 235                 240
Pro Leu Arg Lys Gly Cys Cys Gly Val Thr Glu Asp Gly Lys Asn Ile
                245                 250                 255

Met Cys Trp Leu Asp Leu Gln Pro Ala Lys Ser Val Val Tyr Val Ala
            260                 265                 270

Leu Gly Thr Glu Val Pro Leu Pro Val Glu Gln Met His Glu Leu Ala
        275                 280                 285

Leu Arg Leu Glu Leu Ala Gly Met Gln Phe Leu Trp Ala Leu Arg Lys
    290                 295                 300

Pro Arg Gly Val His Glu Ala Glu Ile Leu Pro Leu Gly Phe Glu Glu
305                 310                 315                 320

Arg Met Xaa Gly Leu Val Thr Thr Gly Leu Ala Pro Gln Ile Asn Ile
                325                 330                 335

Leu Ala His Gly Ala Val Gly Thr Phe Leu Thr His Cys Gly Trp Ser
            340                 345                 350

Leu Thr Ile Glu Gly Leu Leu Phe Gly His Pro Leu Ile Met Leu Pro
        355                 360                 365

Met Phe Gly Asp Gln Gly Pro Asn Ala Arg Leu Met Glu Gly Arg Lys
    370                 375                 380

Val Gly Val Gln Val Pro Arg Asn Glu Gly Asp Gly Ser Phe Asp Arg
385                 390                 395                 400

Glu Gly Val Ala Thr Thr Val Arg Ala Val Thr Val Glu Glu Glu Gly
                405                 410                 415

Lys Arg Ile Phe Thr Ser Asn Ala Lys Lys Met Gln Glu Ile Lys Ala
            420                 425                 430

Asp Thr Glu Cys Gln Glu Arg Tyr Ile Asn Gly Phe Ile Lys Lys Leu
        435                 440                 445

Arg Ser Tyr Lys Glu Pro Asp Leu Ala His Pro Ile Cys Pro Val Thr
    450                 455                 460

Ser Ser Pro Thr His Tyr Glu
465                 470

<210> SEQ ID NO 6
<211> LENGTH: 459
<212> TYPE: PRT
<213> ORGANISM: Hordeum vulgare

<400> SEQUENCE: 6

Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125
```

```
Phe His His Trp Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala
    450                 455

<210> SEQ ID NO 7
<211> LENGTH: 1380
<212> TYPE: DNA
<213> ORGANISM: Hordeum vulgare

<400> SEQUENCE: 7
atggatggta actcctcctc ctcgccgctg catgtggtca tttgtccgtg gctggctctg     60
ggtcacctgc tgccgtgtct ggatattgct gaacgtctgg cgtcacgcgg ccatcgtgtc    120
agttttgtgt ccaccccgcg caacattgcc cgtctgccgc cgctgcgtcc ggctgttgca    180
ccgctggttg atttcgtcgc actgccgctg ccgcatgttg acggtctgcc ggagggtgcg    240
```

```
gaatcgacca atgatgtgcc gtatgacaaa tttgaactgc accgtaaggc gttcgatggt    300
ctggcggccc cgtttagcga atttctgcgt gcagcttgcg cagaaggtgc aggttctcgc    360
ccggattggc tgattgtgga cacctttcat cactgggcgg cggcggcggc ggtggaaaac    420
aaagtgccgt gtgttatgct gctgctgggt gcagcaacgg tgatcgctgg tttcgcgcgt    480
ggtgttagcg aacatgcggc ggcggcggtg ggtaaagaac gtccggctgc ggaagccccg    540
agttttgaaa ccgaacgtcg caagctgatg accacgcaga atgcctccgg catgaccgtg    600
gcagaacgct atttcctgac gctgatgcgt agcgatctgg ttgccatccg ctcttgcgca    660
gaatgggaac cggaaagcgt ggcagcactg accacgctgg caggtaaacc ggtggttccg    720
ctgggtctgc tgccgccgag tccggaaggc ggtcgtggcg tttccaaaga agatgctgcg    780
gtccgttggc tggacgcaca gccggcaaag tcagtcgtgt acgtcgcact gggttcggaa    840
gtgccgctgc gtgcggaaca agttcacgaa ctggcactgg gcctggaact gagcggtgct    900
cgctttctgt gggcgctgcg taaaccgacc gatgcaccgg acgccgcagt gctgccgccg    960
ggtttcgaag aacgtacccg cggccgtggt ctggttgtca cgggttgggt gccgcagatt   1020
ggcgttctgg ctcatggtgc ggtggctgcg tttctgaccc actgtggctg gaactctacg   1080
atcgaaggcc tgctgttcgg tcatccgctg attatgctgc cgatcagctc tgatcagggt   1140
ccgaatgcgc gcctgatgga aggccgtaaa gtcggtatgc aagtgccgcg tgatgaatca   1200
gacggctcgt ttcgtcgcga agatgttgcc gcaaccgtcc gcgccgtggc agttgaagaa   1260
gacggtcgtc gcgtcttcac ggctaacgcg aaaaagatgc aagaaattgt ggccgatggc   1320
gcatgccacg aacgttgtat tgacggtttt atccagcaac tgcgcagtta caaggcgtga   1380
```

<210> SEQ ID NO 8
<211> LENGTH: 488
<212> TYPE: PRT
<213> ORGANISM: Hordeum vulgare

<400> SEQUENCE: 8

```
Met Asp Ala Gly Ser Ser Thr Ala Gly Pro Leu Arg Ile Val Ile Cys
1               5                   10                  15

Pro Trp Leu Ala Phe Gly His Leu Leu Pro Tyr Leu Glu Leu Ala Glu
            20                  25                  30

Arg Leu Ala Ser Arg Gly His Arg Val Ala Phe Val Ser Thr Pro Arg
        35                  40                  45

Asn Leu Ala Arg Leu Pro Pro Pro Ala Ser Pro Cys Ser Val Asp Leu
    50                  55                  60

Val Ala Leu Gln Leu Pro Arg Val Asp Gly Leu Pro Glu Gly Ala Glu
65                  70                  75                  80

Ser Thr Asn Asp Val Pro Asp Glu Met Arg Glu Leu His Trp Lys Ala
                85                  90                  95

Phe Asp Gly Leu Ala Ala Pro Phe Ala Asp Phe Leu Ala Ala Ala Cys
            100                 105                 110

Ala Asp Asp Gly Arg Arg Pro His Trp Ile Ile Ala Asp Cys Phe His
        115                 120                 125

His Trp Ala Ala Ala Ala Ala Leu Asp His Lys Val Pro Cys Ala Val
    130                 135                 140

Leu Leu Pro Thr Ala Ala Met Leu Ala Ala Pro Arg Gln Gln Pro
145                 150                 155                 160

Leu Gly Ser Lys Pro Val Glu Ala Ala Ala Ala Ser Val Leu Gly
                165                 170                 175
```

```
Gln Ala Ala Ala Ala Val Arg Leu Ala Val Pro Ser Tyr Glu Arg Asp
                180                 185                 190

Asp Val Ala Pro Ala Tyr Ala Asp Asp Cys Ala Ser Gly Met Ser Ile
            195                 200                 205

Ala Gln Arg Trp Phe Leu Ala Lys Glu Arg Cys Thr Val Leu Ala Ile
        210                 215                 220

Arg Ser Cys Val Glu Trp Glu Pro Glu Thr Phe Pro Leu Val Glu Ala
225                 230                 235                 240

Leu Leu Gly Lys Pro Val Val Pro Leu Gly Leu Pro Pro Ser Ala
                245                 250                 255

Asp Gly Gly Arg Arg Ala Ala Gly Ser Ser Glu Asp His Val Thr
                260                 265                 270

Leu Arg Trp Leu Glu Glu Gln Pro Pro Asp Ser Val Val Tyr Ile Ala
        275                 280                 285

Leu Gly Ser Glu Val Pro Leu Ser Ile Glu Gln Val His Glu Leu Ala
        290                 295                 300

Leu Gly Leu Glu Leu Ala Gly Thr Arg Phe Leu Trp Ala Leu Arg Lys
305                 310                 315                 320

Pro Ala Gly Ala Val Val Gly Asn Asn Asp Asp Asp Thr Leu Pro Pro
                325                 330                 335

Gly Phe Arg Asp Cys Thr Arg Gly His Gly Leu Val Thr Met Gly Trp
                340                 345                 350

Val Pro Gln Ile Ser Ile Leu Ala His Ala Ala Val Gly Ala Phe Leu
            355                 360                 365

Thr His Cys Gly Arg Asn Ser Leu Ile Glu Gly Leu Leu Phe Gly His
        370                 375                 380

Pro Leu Val Met Leu Pro Ile Phe Gly Asp Gln Gly Pro Asn Ala Arg
385                 390                 395                 400

Gln Met Glu Ala Lys Lys Val Gly Leu Gln Val Ala Arg Asp Asp
                405                 410                 415

Asp Gly Ser Phe Asp Arg His Gly Val Ala Thr Ala Val Arg Ala Val
            420                 425                 430

Met Val Asp Gly Glu Ala Arg Arg Gly Phe Val Ala Asn Ala Ile Lys
        435                 440                 445

Met Gln Ala Ile Val Ala Asp Lys Glu Arg His Glu Arg Tyr Ile Asp
450                 455                 460

Gly Phe Val Gln Gln Leu Arg Ser Tyr Leu Gln Ala Thr Asp Asp Leu
465                 470                 475                 480

Thr Thr Ala Thr Pro Asn Ser Ser
                485

<210> SEQ ID NO 9
<211> LENGTH: 808
<212> TYPE: PRT
<213> ORGANISM: Arabidopsis thaliana

<400> SEQUENCE: 9

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60
```

```
Glu Gly Gly Pro Phe Phe Asp Leu Leu Lys Ser Thr Gln Glu Ala Ile
 65                  70                  75                  80

Val Leu Pro Pro Trp Val Ala Leu Ala Val Arg Pro Arg Pro Gly Val
                 85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
            260                 265                 270

Gly Arg Val Pro Met Val Phe Asn Val Val Ile Leu Ser Pro His Gly
        275                 280                 285

Tyr Phe Ala Gln Asp Asn Val Leu Gly Tyr Pro Asp Thr Gly Gly Gln
290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
450                 455                 460

Phe Thr Ala Asp Ile Phe Ala Met Asn His Thr Asp Phe Ile Ile Thr
465                 470                 475                 480
```

```
Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Lys Arg Arg Leu Thr
    530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Ala Asn Leu Val Val
        595                 600                 605

Val Gly Gly Asp Arg Arg Lys Glu Ser Lys Asp Asn Glu Glu Lys Ala
    610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
            660                 665                 670

Leu Tyr Glu Ala Phe Gly Leu Thr Val Val Glu Ala Met Thr Cys Gly
        675                 680                 685

Leu Pro Thr Phe Ala Thr Cys Lys Gly Gly Pro Ala Glu Ile Ile Val
    690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu Ala Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 10
<211> LENGTH: 2427
<212> TYPE: DNA
<213> ORGANISM: Arabidopsis thaliana

<400> SEQUENCE: 10
atggcaaacg ctgaacgtat gataacgcgc gtccacagcc aacgtgagcg tttgaacgaa      60
acgcttgttt ctgagagaaa cgaagtcctt gccttgcttt ccagggttga agccaaaggt     120
aaaggtattt tacaacaaaa ccagatcatt gctgaattcg aagctttgcc tgaacaaacc     180
cggaagaaac ttgaaggtgg tcctttcttt gaccttctca aatccactca ggaagcaatt     240
```

```
gtgttgccac catgggttgc tctagctgtg aggccaaggc ctggtgtttg ggaatactta    300
cgagtcaatc tccatgctct tgtcgttgaa gaactccaac ctgctgagtt tcttcatttc    360
aaggaagaac tcgttgatgg agttaagaat ggtaatttca ctcttgagct tgatttcgag    420
ccattcaatg cgtctatccc tcgtccaaca ctccacaaat acattggaaa tggtgttgac    480
ttccttaacc gtcatttatc ggctaagctc ttccatgaca aggagagttt gcttccattg    540
cttaagttcc ttcgtcttca cagccaccag ggcaagaacc tgatgttgag cgagaagatt    600
cagaacctca acactctgca acacaccttg aggaaagcag aagagtatct agcagagctt    660
aagtccgaaa cactgtatga agagtttgag gccaagtttg aggagattgg tcttgagagg    720
ggatggggag acaatgcaga gcgtgtcctt gacatgatac gtcttctttt ggaccttctt    780
gaggcgcctg atccttgcac tcttgagact tttcttggaa gagtaccaat ggtgttcaac    840
gttgtgatcc tctctccaca tggttacttt gctcaggaca atgttcttgg ttaccctgac    900
actggtggac aggttgttta cattcttgat caagttcgtg ctctggagat agagatgctt    960
caacgtatta agcaacaagg actcaacatt aaaccaagga ttctcattct aactcgactt   1020
ctacctgatg cggtaggaac tacatgcggt gaacgtctcg agagagttta tgattctgag   1080
tactgtgata ttcttcgtgt gcccttcaga acagagaagg gtattgttcg caaatggatc   1140
tcaaggttcg aagtctggcc atatctagag acttacaccg aggatgctgc ggttgagcta   1200
tcgaaagaat tgaatggcaa gcctgacctt atcattggta actacagtga tggaaatctt   1260
gttgcttctt tattggctca caaacttggt gtcactcagt gtaccattgc tcatgctctt   1320
gagaaaacaa gtaccccgga ttctgatatc tactggaaga agcttgacga caagtaccat   1380
ttctcatgcc agttcactgc ggatattttc gcaatgaacc acactgattt catcatcact   1440
agtactttcc aagaaattgc tggaagcaaa gaaactgttg gcagtatgaa agccacaca    1500 gcctttactc ttcccggatt gtatcgagtt gttcacggga ttgatgtgtt tgatcccaag   1560
ttcaacattg tctctcctgg tgctgatatg agcatctact tcccttacac agaggagaag   1620
cgtagattga ctaagttcca ctctgagatc gaggagctcc tctacagcga tgttgagaac   1680
aaagagcact atgtgtgct caaggacaag aagaagccga ttctcttcac aatggctagg   1740
cttgatcgtg tcaagaactt gtcaggtctt gttgagtggt acgggaagaa cacccgcttg   1800
cgtgagctag ctaacttggt tgttgttgga ggagacagga ggaaagagtc aaaggacaat   1860
gaagagaaag cagagatgaa gaaaatgtat gatctcattg aggaatacaa gctaaacggt   1920
cagttcaggt ggatctcctc tcagatggac cgggtaagga acggtgagct gtaccggtac   1980
atctgtgaca ccaagggtgc ttttgtccaa cctgcattat atgaagcctt tgggttaact   2040
gttgtggagg ctatgacttg tggtttaccg actttcgcca cttgcaaagg tggtccagct   2100
gagatcattg tgcacggtaa atcgggtttc cacattgacc cttaccatgg tgatcaggct   2160
gctgatactc ttgctgattt cttcaccaag tgtaaggagg atccatctca ctgggatgag   2220
atctcaaaag gagggcttca gaggattgag gagaaataca cttggcaaat ctattcacag   2280
aggctcttga cattgactgg tgtgtatgga ttctggaagc atgtctcgaa ccttgaccgt   2340
cttgaggctc gccgttacct tgaaatgttc tatgcattga agtatcgccc attggctcag   2400
gctgttcctc ttgcacaaga tgattga                                       2427
```

<210> SEQ ID NO 11
<211> LENGTH: 458
<212> TYPE: PRT
<213> ORGANISM: Stevia rebaudiana

<400> SEQUENCE: 11

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
                115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
                370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
```

```
                    405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 12
<211> LENGTH: 1377
<212> TYPE: DNA
<213> ORGANISM: Stevia rebaudiana

<400> SEQUENCE: 12
atggagaata agacagaaac aaccgtaaga cggaggcgga ggattatctt gttccctgta       60
ccatttcagg gccatattaa tccgatcctc aattagcaa acgtcctcta ctccaaggga      120
ttttcaataa caatcttcca tactaacttt aacaagccta aaacgagtaa ttatcctcac      180
tttacattca ggttcattct agacaacgac cctcaggatg agcgtatctc aaatttacct      240
acgcatggcc ccttggcagg tatgcgaata ccaataatca atgagcatgg agccgatgaa      300
ctccgtcgcg agttagagct tctcatgctc gcaagtgagg aagacgagga gtttcgtgc       360 ctaataactg atgcgctttg gtacttcgcc caatcagtcg cagactcact gaatctacgc      420
cgtttggtcc ttatgacaag ttcattattc aactttcacg cacatgtatc actgccgcaa      480
tttgacgagt tgggttacct ggacccggat gacaaaacgc gattggagga caagcgtcg       540 ggcttcccca tgctgaaagt caagatatt aagagcgctt atagtaattg gcaaattctg      600
aaagaaattc tcggaaaaat gataaagcaa accaaagcgt cctctggagt aatctggaac      660
tccttcaagg agttagagga atctgaactt gaaacggtca tcagagaaat ccccgctccc      720
tcgttcttaa ttccactacc caagcacctt actgcaagta gcagttccct cctagatcat      780
gaccgaaccg tgtttcagtg gctggatcag caaccccgt cgtcagttct atatgtaagc      840
tttgggagta cttcggaagt ggatgaaaag gacttcttag agattgcgcg agggctcgtg      900
gatagcaaac agagcttcct gtgggtagtg agaccgggat tcgttaaggg ctcgacgtgg      960
gtcgagccgt tgccagatgg ttttctaggg gagagaggga gaatcgtgaa atgggttcca     1020
cagcaagagg ttttggctca cggagctata ggggcctttt ggacccactc tggttggaat     1080
tctactcttg aaagtgtctg tgaaggcgtt ccaatgatat tttctgattt tgggcttgac     1140
cagcctctaa acgtcgcta tatgtctgat gtgttgaagg ttggcgtgta cctggagaat     1200
ggttgggaaa gggggaaat tgccaacgcc atacgccggg taatggtgga cgaggaaggt     1260
gagtacatac gtcagaacgc tcgggtttta aaacaaaaag cggacgtcag ccttatgaag     1320
ggaggtagct cctatgaatc cctagaatcc ttggtaagct atatatcttc gttataa       1377
```